United States Patent
Jones et al.

(10) Patent No.: US 8,658,165 B2
(45) Date of Patent: Feb. 25, 2014

(54) METHOD OF TREATING ABERRANT MUCUS PRODUCTION IN RESPIRATORY DISEASE

(75) Inventors: Carol Elizabeth Jones, Horsham (GB); Alan Jackson, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/568,300

(22) Filed: Aug. 7, 2012

(65) Prior Publication Data

US 2013/0034567 A1    Feb. 7, 2013

Related U.S. Application Data

(62) Division of application No. 12/674,964, filed on Feb. 24, 2010, now abandoned.

(30) Foreign Application Priority Data

Aug. 24, 2007  (EP) .................................. 07114972

(51) Int. Cl.
*A61K 39/395* (2006.01)
*C07K 16/28* (2006.01)

(52) U.S. Cl.
USPC ................. 424/130.1; 424/143.1; 530/387.1; 530/388.22

(58) Field of Classification Search
None
See application file for complete search history.

(56) References Cited

U.S. PATENT DOCUMENTS

2005/0208527 A1   9/2005  Steffansson et al.

FOREIGN PATENT DOCUMENTS

WO    0164877 A2    9/2001
WO    0205842 A2    1/2002

OTHER PUBLICATIONS

Dammann et al.;"Role of Neuregulin-1β in the Developing Lung"; American Journal of Respiratory and Critical Care Medicine (2003); 167(12); 171.
Funes et al.; "The Mucin Muc4 Potentiates Neuregulin Signaling by Increasing the Cell-surface Populations of ErbB2 and ErbB3"; Journal of Biological Chemistry (2006); 281(28); 19310.
Gollamundi et al.; "Autocrine activation of ErbB2/ErbB3 receptor complex by NRG-1 in non-small cell lung cancer cell lines"; Lung Cancer (2004); 43; 135.
Jones et al.; "Binding Specificities and Affinities of egf Domains for ErbB receptors"; FEBS Letters (1999); 47; 227.
Kumar et al.; "Effects of ANticytokine Therapy in a Mouse Model of Chronic Asthma"; American Journal of Respiratory and Critical Care Medicine (2004); 170; 1043.
Nethery et al.; "Expression of Mutant Human Epidermal Receptor 3 Attenuates Lung Fibrosis and Improves Survival in Mice"; Journal of Applied Physiology (2005); 99; 298.
Vermeer et al.; "Differentiation of Human Airway Epithelia is Dependent on ErbB2"; American Journal of Physiology—Lung, Cell, and Molecular Physiology; 291; L175, (2006).

*Primary Examiner* — Christine J Saoud
*Assistant Examiner* — Jon M Lockard
(74) *Attorney, Agent, or Firm* — Karen A. Lacourse

(57) ABSTRACT

The present invention relates to modulators of the Neuregulin (NRG) family, particularly NRG1 and more particularly NRG1β, and most particularly NRG1β1. The present invention also relates to the use of such modulators to inhibit goblet cell hyperplasia and therefore also relates to the use of such modulators in the treatment or prevention of human diseases and disorders featuring pathological mucus production such as COPD, CF, chronic bronchitis and asthma.

5 Claims, 10 Drawing Sheets

SEQUENCE LISTING

```
<160> NUMBER OF SEQ ID NOS: 21

<210> SEQ ID NO 1
<211> LENGTH: 23
<212> TYPE: DNA
<213> ORGANISM: Artificial sequence
<220> FEATURE:
<223> OTHER INFORMATION: Synthetic sequence: Primer TransFor

<400> SEQUENCE: 1
ttacagtggc tgtattctgc tgg                                           23

<210> SEQ ID NO 2
<211> LENGTH: 23
<212> TYPE: DNA
<213> ORGANISM: Artificial sequence
<220> FEATURE:
<223> OTHER INFORMATION: Synthetic sequence: Primer TransRev
```

```
<400> SEQUENCE: 2
tgctgttctc atggaagcta tgg                                              23

<210> SEQ ID NO 3
<211> LENGTH: 19
<212> TYPE: DNA
<213> ORGANISM: Artificial sequence
<220> FEATURE:
<223> OTHER INFORMATION: Synthetic sequence: Primer NRG1beta1For

<400> SEQUENCE: 3
caagcatctt gggattgaa                                                   19

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Primer NRG1Rev

<400> SEQUENCE: 4
tgtttcgttc tgaccgaagg                                                  20

<210> SEQ ID NO 5
<211> LENGTH: 23
<212> TYPE: DNA
<213> ORGANISM: Artificial sequence
<220> FEATURE:
<223> OTHER INFORMATION: Synthetic sequence: Primer Muc5acFor

<400> SEQUENCE: 5
cagccgagag gagggtttga tct                                              23

<210> SEQ ID NO 6
<211> LENGTH: 23
<212> TYPE: DNA
<213> ORGANISM: Artificial sequence
<220> FEATURE:
<223> OTHER INFORMATION: Synthetic sequence: Primer Muc5acRev

<400> SEQUENCE: 6
agtctctctc cgctcctctc aat                                              23

<210> SEQ ID NO 7
<211> LENGTH: 21
<212> TYPE: DNA
<213> ORGANISM: Artificial sequence
<220> FEATURE:
<223> OTHER INFORMATION: Synthetic sequence: Primer Muc5bFor

<400> SEQUENCE: 7
aggaagacca gtgtgtttgt c                                                21

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Primer Muc5bRev

<400> SEQUENCE: 8
gtcctcattg aagaagggct g                                                21
```

-continued

```
<210> SEQ ID NO 9
<211> LENGTH: 22
<212> TYPE: DNA
<213> ORGANISM: Artificial sequence
<220> FEATURE:
<223> OTHER INFORMATION: Synthetic sequence: Primer Mmbeta-actinFor

<400> SEQUENCE: 9
tgtgatggtg ggaatgggtc ag                                              22

<210> SEQ ID NO 10
<211> LENGTH: 22
<212> TYPE: DNA
<213> ORGANISM: Artificial sequence
<220> FEATURE:
<223> OTHER INFORMATION: Synthetic sequence: Primer Mmbeta-actinRev

<400> SEQUENCE: 10
tttgatgtca cgcacgattt cc                                              22

<210> SEQ ID NO 11
<211> LENGTH: 13
<212> TYPE: PRT
<213> ORGANISM: Homo sapiens

<400> SEQUENCE: 11

Ser Trp Tyr Asn Gly His Arg Pro Glu Pro Gly Leu Gly
1               5                   10

<210> SEQ ID NO 12
<211> LENGTH: 22
<212> TYPE: DNA
<213> ORGANISM: Artificial sequence
<220> FEATURE:
<223> OTHER INFORMATION: Synthetic sequence: Primer ErbB1F

<400> SEQUENCE: 12
gtcctcattg ccctcaacac ag                                              22

<210> SEQ ID NO 13
<211> LENGTH: 22
<212> TYPE: DNA
<213> ORGANISM: Artificial sequence
<220> FEATURE:
<223> OTHER INFORMATION: Synthetic sequence: Primer ErbB1R

<400> SEQUENCE: 13
ccattgggac agcttggatc ac                                              22

<210> SEQ ID NO 14
<211> LENGTH: 21
<212> TYPE: DNA
<213> ORGANISM: Artificial sequence
<220> FEATURE:
<223> OTHER INFORMATION: Synthetic sequence: Primer ErbB2F

<400> SEQUENCE: 14
cagttaccag tgccaatatc c                                               21

<210> SEQ ID NO 15
<211> LENGTH: 19
<212> TYPE: DNA
<213> ORGANISM: Artificial sequence
<220> FEATURE:
<223> OTHER INFORMATION: Synthetic sequence: Primer ErbB2R
```

```
<400> SEQUENCE: 15
ttgtgcagaa ttcgtcccc                                           19

<210> SEQ ID NO 16
<211> LENGTH: 19
<212> TYPE: DNA
<213> ORGANISM: Artificial sequence
<220> FEATURE:
<223> OTHER INFORMATION: Synthetic sequence: Primer ErbB3F

<400> SEQUENCE: 16
actctgaatg gcctgagtg                                           19

<210> SEQ ID NO 17
<211> LENGTH: 20
<212> TYPE: DNA
<213> ORGANISM: Artificial sequence
<220> FEATURE:
<223> OTHER INFORMATION: Synthetic sequence: Primer ErbB3R

<400> SEQUENCE: 17
caaacttccc atcgtagacc                                          20

<210> SEQ ID NO 18
<211> LENGTH: 19
<212> TYPE: DNA
<213> ORGANISM: Artificial sequence
<220> FEATURE:
<223> OTHER INFORMATION: Synthetic sequence: Primer ErbB4F

<400> SEQUENCE: 18
accagcattg agcacaacc                                           19

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Primer ErbB4R

<400> SEQUENCE: 19
cgtccacatc ctgaactacc                                          20

<210> SEQ ID NO 20
<211> LENGTH: 24
<212> TYPE: DNA
<213> ORGANISM: Artificial sequence
<220> FEATURE:
<223> OTHER INFORMATION: Synthetic sequence: Primer GAPDHF

<400> SEQUENCE: 20
ccacccatgg caaattccat ggca                                     24

<210> SEQ ID NO 21
<211> LENGTH: 24
<212> TYPE: DNA
<213> ORGANISM: Artificial sequence
<220> FEATURE:
<223> OTHER INFORMATION: Synthetic sequence: Primer GAPDHR

<400> SEQUENCE: 21
tctagacggc aggtcaggtc cacc                                     24
```

METHOD OF TREATING ABERRANT MUCUS PRODUCTION IN RESPIRATORY DISEASE

1. FIELD OF THE INVENTION

Figure 1:
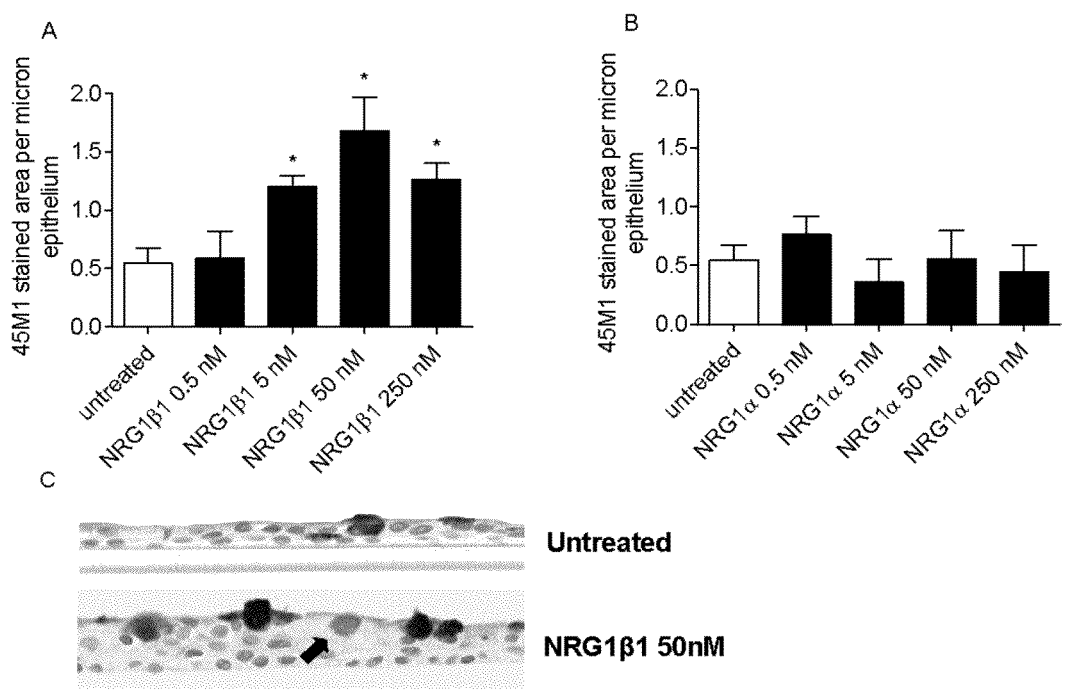

The present invention concerns compounds, compositions and methods for neutralising the biological activity of members of the Neuregulin (NRG) family in the treatment of diseases and disorders. In particular the invention concerns antagonists which bind with and neutralise the biological activity of Neuregulin-1 (NRG1) and isoforms thereof in the treatment of human diseases and disorders. Other aspects, objects and advantages of the present invention will be apparent from the description below.

2. BACKGROUND OF THE INVENTION

Airway mucus hypersecretion has been linked to several of the pathological features of respiratory diseases such as asthma [Aikawa et al, 1992], chronic obstructive pulmonary disease (COPD) [Vestbo, 2002] and cystic fibrosis (CF) [Boucher, 2002]. Indeed, mucus hypersecretion has been linked to an increase in frequency and duration of infection, decline in lung function and increase in morbidity and mortality in respiratory diseases [Vestbo, 2002; Prescott et al, 1995; Vestbo et al, 1996]. Whilst in the large airways mucus is produced by goblet cells and submucosal glands, in the small airways the only source of mucus is the goblet cell [Rogers, 2003]. The mucins MUC5AC and MUC5B are major components of airway mucus secretions in respiratory diseases such as asthma, COPD and CF [Williams et al, 2006; Rose and Voynow, 2006; Rogers, 2003]. Mucus hypersecretion is a feature of asthma where morphometric analysis of lungs from patients who died from a severe acute asthma attack showed increases in goblet cell numbers and mucus in the airway lumen [Aikawa et al, 1992]. Mucus plugging of the airway lumen has been reported as a major contributing cause to fatal asthma in most patients [Kuyper et al, 2003; Hays and Fahay, 2003]. MUC5AC expression is increased in status asthmaticus compared to normal individuals and is localized to the surface epithelium, lumen and goblet cells [Gronenberg et al, 2002a]. Increased numbers of goblet cells have also been reported in subjects with mild to moderate asthma compared to healthy individuals and levels of secreted mucin are reported to be higher in the airways of patients with moderate asthma [Ordonez et al, 2001]. Additionally, increased MUC5AC mucin staining of goblet cells of subjects with asthma compared to healthy individuals has bee reported [Ordonez et al, 2001]. The mucin MUC5B is also produced by some airway surface goblet cells in asthmatics [Gronenberg et al, 2002a]. The progression of COPD has been reported to be strongly associated with accumulation of mucus in the lumen of the small airways [Hogg et al, 2004]. In individuals with COPD increased expression of MUC5AC has been described within the bronchiolar epithelium in addition to increased levels of MUC5B within the bronchiolar lumen [Caramori et al, 2004]. MUC5B has also been reported as a major mucin in sputum of patients with COPD in a separate study [Kirkham et al, 2002]. The increased mucus observed in the lumen of bronchioles in COPD patients has been suggested to contribute to obstruction of the peripheral airways in COPD [Caramori et al, 2004]. Increased numbers of goblet cells in the bronchiolar epithelium of patients with COPD and chronic bronchitis have also been described [Saetta et al, 2000]. In CF mucus hypersecretion is associated with airflow obstruction and, in fatal cases, occlusion of the small airways [Williams et al, 2006]. Excessive mucus also appears to contribute to CF morbidity by increasing the frequency and severity of pulmonary infections [Williams et al, 2006]. Although concentrations of secreted mucins MUC5AC and MUC5B have been reported to be decreased in CF subjects compared with normals [Henke et al, 2004], MUC5AC and MUC5B are increased in sputum of CF patients during exacerbations [Henke et al, 2007]. Goblet cell hyperplasia resulting from increased numbers of MUC5AC-positive cells, have been reported to be increased in cystic fibrosis lung [Gronenberg et al, 2002b].

Whilst IL-13 has been shown to influence MUC5AC gene and protein expression in vitro and in vivo [Wills-Karp et al, 1998; Zhu et al, 1999; Kuperman et al, 2002; Atherton, Jones and Danahay, 2003], it has no effect on the mucin MUC5B. The mediators of MUC5B production are not well characterized.

Neuregulins are signalling proteins that mediate multiple cell-cell interactions via the receptor tyrosine kinases of the ERB family. At least 15 different isoforms of Neuregulin-1 (NRG1) exist as a result alternative splicing [Falls, 2003]. Two of these isoforms, NRG1a and NRG1β1, differ in the C-terminal portion of the EGF-like domain [Holmes et al, 1992]. NRG1 is thought to bind to ErbB3 or ERRB4 which form heterodimers with ErbB2 [Falls, 2003]. NRG1β1 binds to ErbB3 with 100-fold higher affinity than NRG1a. NRG1β1 also has a 100-fold greater affinity for the ErbB2/ErbB3 heterodimer than ErbB3 homodimers [Jones et al, 1999]. ErbB3 lacks tyrosine kinase activity, but dimerisation with ErbB2 results in the formation of an active heterodimer which can mediate downstream signals [Citri, Skaria and Yarden, 2003]. A role for NRG1 and the ErbB2 and 3 receptors in human lung development have previously been suggested through immunohistochemical and functional studies on fetal lung tissue [Patel et al, 2000]. NRG1β1 is secreted from fetal lung fibroblasts and stimulates type II cell surfactant synthesis and is therefore proposed to control fetal lung maturation through mesenchymal-epithelial interactions [Dammam et al, 2003]. More recently the NRG 1a isoform has been suggested to play a role in epithelial wound repair and remodeling in the airways [Vermeer et al, 2003]. In this study the ErbB2 receptor was shown to been expressed on the basolateral surface of differentiated epithelial cells and NRG1a ligand expressed at the apical surface. Consequently ligand receptor interactions are not thought to take place until an epithelial injury has occurred. Expression of NRG (sometimes referred to as Heuregulin, "HRG") has been examined in bronchial tissue from COPD patients and higher expression observed in intact epithelium of subjects with COPD compared to those without COPD [de Boer et al, 2006]. However, in the study of de Boer et al. the specific isoform of NRG1 investigated was not stated.

All publications, including patent applications, cited in the present specification and any specification from which the present application claims priority are expressly incorporated herein by reference in their entirety.

3. SUMMARY OF THE INVENTION

The present inventions based, at least in part, on the observation that NRG-1, and in particular the isoform NRG1β1 promotes MUC5AC and MUC5B protein expression and therefore suggests a role in goblet cell formation.

Accordingly, in a first aspect of the present invention there is provided a method of inhibiting goblet cell formation which method comprises providing a binding compound which neutralizes the biological activity of NRG-1, e.g. NRG1β isoform, particularly NRG1β1 (and in particular human NRG1β1).

In a second aspect of the present invention there is provided a method of screening for a binding compound capable of neutralizing NRG-1 e.g. NRG1β1 biological activity.

In a third aspect of the present invention there is provided a pharmaceutical composition comprising (or consisting essentially of) a binding compound which neutralizes NRG-1, e.g. NRG1β1 (particularly human NRG1β1) biological activity.

In a fourth aspect of the present invention there is provided a method of inhibiting goblet cell formation in a mammalian patient which method comprises administering to said patient a therapeutically effective amount of a binding compound which neutralizes the biological activity of NRG-1, e.g. NRG1β1.

In a fifth aspect of the invention there is provided a method of inhibiting deleterious mucus production in a mammalian patient in clinical need thereof which method comprises administering to said patient a therapeutically effective amount of a binding compound which neutralizes the biological activity of NRG-1, e.g. NRGβ1.

In a sixth aspect there is provided a method of treating a disease or disorder selected from the group consisting of; COPD, CF, chronic bronchitis and asthma (particularly moderate to severe asthma) in a human patient which method comprises administering to said patient a therapeutically effective amount of a human or humanized antibody (of e.g. a IgG isotype such as IgG1 or IgG4) which neutralizes the biological activity of NRG1β1 (by for example binding with NRG1β1 and inhibiting the interaction between NRG1β1 and ErbB2/Erb B3 heterodimer).

These and other aspects of the present invention are described in more detail below.

4. DETAILED DESCRIPTION OF THE INVENTION

In the description that follows in section 4, reference to various proteins, isoforms thereof and treatment of diseases/ disorders are in relation to human proteins, isoforms thereof and human diseases and disorders. Thus "NRG-1", "NRG1a" and "NRG1β1" are to be construed as referring to human NRG-1 etc. In the embodiments described below, reference to "NRG1" and "NRG1β1" may be taken to refer to all forms of the respective protein and additionally and individually, to soluble and membrane bound forms and the reader of this specification may assume that each embodiment is intended to be construed as such. Therefore, unless specified otherwise, in each embodiment described below refers to three embodiments, firstly to all forms of the respective protein, secondly to any membrane bound form and thirdly to soluble forms of the respective protein.

4.1 Binding Compounds

In one aspect of the present invention, there is provided a binding compound that neutralizes the biological activity of a NRG1 protein.

In some embodiments, the binding compound binds with and neutralizes the ability of NRG1β1 to promote expression of MUC5AC and MUC5B on epithelial cells (e.g. goblet cells). Such binding compounds may bind with and inhibit NRG1β1 binding with its cognate receptor e.g. ErbB2 and/or ErbB3, preferably the ErbB2/ErbB3 heterodimer. In such embodiments, the binding compound maybe a low molecular weight chemical entity capable of binding with a NRG-1 protein such as NRG-1β1 and thereby neutralize its biological activity by e.g. inhibiting the interaction between the protein and its cognate receptor, e.g. ErbB2 and/or ErbB3. In other such embodiments, the binding compound maybe a therapeutic protein such as an antibody capable of binding with and inhibiting the interaction between the NRG-1 protein (e.g. NRG-1β1) and its cognate receptor (e.g. ErbB2 and/or ErbB3). These embodiments are described in more detail below. In another embodiment, the binding compound may bind with ADAM-17 and inhibit the activity thereof, to, in turn inhibit the formation of soluble NRG1β1 from its membrane bound precursor form.

In another embodiment, the binding compound may inhibit the expression of NRG-1, e.g. NRG-1β1 and thereby neutralize the ability of NRG1 to promote MUC5AC and MUC5B protein expression on epithelial cells. In these embodiments, the binding compound may inhibit the expression of NRG-1 (e.g. NRG-1β1) at the level of transcription and/or translation. For example, the binding compound maybe an antisense oligonucleotide capable of binding with the complementary region of the NRG-1 gene and thereby inhibit its transcription. In other such embodiments, the binding compound maybe a short interfering RNA (siRNA) capable of inhibiting the translation of a RNA compound capable of encoding a NRG-1 (e.g. NRG-1β1) protein. These embodiments are described in some more detail below.

4.1—Therapeutic Proteins

A therapeutic protein of the present invention maybe an antibody, Adnectin, Ankyrin, Maxybody/Avimer, Affibody, anticalin, or Affilin.

4.1.1.—Antibodies

Antibodies of the present invention maybe in any of a number of formats well known to the skilled person. These formats include intact antibodies, various antibody fragments and other engineered formats as described below. In preferred forms, antibodies of the present invention are provided as a monoclonal population.

4.1.1.1—Intact Antibodies

Intact antibodies include heteromultimeric glycoproteins comprising at least two heavy and two light chains. Aside from IgM, intact antibodies are usually heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two type called Kappa or Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, lgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from other chain contribute to the formation of the antigen binding site of antibodies. The constant regions are not directly involved in the binding of the antibody to the antigen but exhibit various effector functions such as participation in antibody dependent cell-mediated cytoxicity (ADCC), phagocytosis via binding to Fcγ receptor, half-life/clearance rate via neonatal Fc receptor (FcRn) and complement dependent cytoxicity via the C1q component of the complement cascade.

Thus in one embodiment of the invention there is provided an intact therapeutic antibody capable of binding NRG1 (e.g. NRG 1β1) and neutralizing the biological activity thereof. In particular the intact therapeutic antibody binds with NRG1 (e.g. NRG1β1 and inhibits the interaction between NRG1 (or NRG1β1) and its cognate receptor ErbB2 and/or ErbB3, particularly the ErbB2/ErbB3 heterodimer. In typical embodiments, the antibody comprises a primate, and in particular a human constant region of an IgG isotype, e.g. IgG1 or IgG4 and is a human, humanised or chimeric antibody as described below In another embodiment, there is provided an intact therapeutic antibody capable of preferentially binding NRG1β1 (compared with NRG1a) and neutralizing the biological activity thereof. In particular the intact therapeutic antibody preferentially binds with NRG1β1 and inhibits the interaction between NRG1β1 and its cognate receptor ErbB2 and/or ErbB3, particularly the ErbB2/ErbB3 heterodimer. In preferred forms, the intact therapeutic antibody comprises a primate, and in particular a human constant region of an IgG isotype, e.g. IgG1 or IgG4 and is a human, humanised or chimeric antibody as described below. The term "preferentially binds" and grammatical variations thereof used throughout this specification refers to the ability of the therapeutic protein (e.g. antibody) to bind NRG1β1 with a higher affinity (at least 2 fold) than it binds NRG1a. The preferentially binding protein however is capable of neutralising to some significant degree the same shared biological activity of both NRG1β1 and NRG1a.

In another embodiment, there is provided an intact therapeutic antibody capable of specifically binding NRG1β1 (compared with NRG1a) and neutralizing the biological activity thereof. In particular the intact therapeutic antibody specifically binds with NRG 1β1 and inhibits the interaction between NRG1β1 and its cognate receptor ErbB2 and/or ErbB3, particularly the ErbB2/ErbB3 heterodimer. In preferred forms, the intact therapeutic antibody comprises a primate, and in particular a human constant region of an IgG isotype, e.g. IgG1 or IgG4 and is a human, humanised or chimeric antibody as described below. The term "specifically binds" and grammatical variations thereof used throughout the present specification refers to the ability of the therapeutic protein (e.g. antibody) to bind with NRG1β1 with a higher (e.g. at least 5 fold higher) binding affinity than it does to NRG1a. The specifically binding therapeutic protein is capable of neutralising NRG1β1 biological activity but does not, to any significant degree, neutralise the same shared biological activity of NRG1a.

In one embodiment of the invention there is provided an intact therapeutic antibody capable of binding membrane bound NRG1 (e.g. NRG1β1) and neutralizing the biological activity thereof. In particular the intact therapeutic antibody binds with membrane NRG1 (e.g. NRG1β1 and inhibits the interaction between NRG1 (or NRG1β1) and its cognate receptor ErbB2 and/or ErbB3, particularly the ErbB2/ErbB3 heterodimer. The intact therapeutic antibody may, for example, bind with membrane bound NRG1 (e.g. NRG1β1) and inhibit formation of soluble NRG1 (e.g. NRG1β1) therefrom by, e.g. inhibiting cleavage of membrane bound NRG1 (e.g. NRG1β1) or by promoting recycling of membrane NRG1 (e.g. NRG1β1). In typical embodiments, the antibody comprises a primate, and in particular a human constant region of an IgG isotype, e.g. IgG1 or IgG4 and is a human, humanised or chimeric antibody.

In another embodiment of the invention there is provided an intact therapeutic antibody capable of binding soluble NRG1 (e.g. NRG1β1) and neutralizing the biological activity thereof. In particular the intact therapeutic antibody binds with soluble NRG1 (e.g. NRG1β1 and inhibits the interaction between NRG1 (or NRG1β1) and its cognate receptor ErbB2 and/or ErbB3, particularly the ErbB2/ErbB3 heterodimer. In typical embodiments, the antibody comprises a primate, and in particular a human constant region of an IgG isotype, e.g. IgG1 or IgG4 and is a human, humanised or chimeric antibody.

4.1.1.1.1 Human Antibodies

Human antibodies may be produced by a number of methods known to those of skill in the art. Human antibodies can be made by the hybridoma method using human myeloma or mouse-human heteromyeloma cells lines see Kozbor J. Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu. Rev. Immunol. 12, 433-455, Green L L (1999), J. Immunol. Methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D M (1996) Nature Biotechnol. 14, 845-851. Mendez M J, 1997, Nature Genetics, 15, 146-156). Upon antigen challenge such mice are capable of producing a repertoire of human antibodies from which antibodies of interest can be selected. Of particular note is the Trimera™ system (see Eren R et al, (1988) Immunology 93:154-161) where human lymphocytes are transplanted into irradiated mice, the Selected Lymphocyte Antibody System (SLAM, see Babcook et al, PNAS (1996) 93: 7843-7848) where human (or other species) lymphocytes are effectively put through a massive pooled in vitro antibody generation procedure followed by deconvulated, limiting dilution and selection procedure and the Xenomouse™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13: 3245-3260. According to this technique antibody V domain genes are cloned in frame into either a major or minor coat of protein gene of a filamentous bacteriophage such as M13 or fd and displayed (usually with the aid of a helper phage) as function antibody fragments on the surface of the phage particle. Selections based on the function properties of the antibody result in selection of the gene encoding the antibody exhibiting these properties. The phage display technique can be used to select antigen specific antibodies from libraries made from human B cells taken from individuals afflicted with a disease or disorder described above or alternatively from unimmunized human donors (see Marks; J Mol Bio 222, 581-591, 1991). Where an intact human antibody is desired comprising an Fc domain it is necessary redone the phage displayed derived fragment into a mammalian expression vectors comprising the desired constant regions and establishing stable expressing cell lines.

The technique of affinity maturation (Marks; Bio/technol 10, 779-783 (1992)) may be used to provide binding affinity wherein the affinity of the primary human antibody is improved by sequentially replacing the H and L chain V regions with naturally occurring variants and selecting on the basis of improved binding affinities. Variants of this technique such as 'epitope imprinting' are now also available, see WO 93/06213. See also Waterhouse; Nucl Acids Res 21, 2265-2266 (1993).

Thus in one embodiment of the invention there is provided an intact therapeutic human antibody capable of binding NRG1 (e.g. NRG1β1) and neutralizing the biological activity thereof. In particular the intact therapeutic human antibody binds with NRG1β1 and inhibits the interaction between NRG1β1 and its cognate receptor ErbB2 and/or ErbB3, particularly the ErbB2/ErbB3 heterodimer. In typical embodiments the intact therapeutic human antibody comprises a constant region of an IgG isotype, e.g. IgG1 or IgG4.

In another embodiment, there is provided an intact therapeutic human antibody capable of preferentially binding NRG1β1 (compared with NRG1a) and neutralizing the biological activity thereof. In particular the intact therapeutic human antibody preferentially binds with NRG1β1 and inhibits the interaction between NRG1 and its cognate receptor ErbB2 and/or ErbB3, particularly ErbB2/ErbB3 heterodimer. In preferred forms, the intact therapeutic human antibody comprises a constant region of an IgG isotype, e.g. IgG1 or IgG4.

In another embodiment, there is provided an intact therapeutic human antibody capable of specifically binding NRG1β1 (compared with NRG1a) and neutralizing the biological activity thereof. In particular the intact therapeutic human antibody specifically binds with NRG1β1 and inhibits the interaction between NRG1β1 and its cognate receptor ErbB2 and/or ErbB3. In preferred forms, the intact therapeutic human antibody comprises a constant region of an IgG isotype, e.g. IgG1 or IgG4.

4.1.1.1.2 Chimaeric and Humanised Antibodies

The use of intact non-human antibodies in the treatment of human diseases or disorders carries with it the potential for the now well established problems of immunogenicity, that is the immune system of the patient may recognises the non-human intact antibody as non-self and mount a neutralising response. This is particularly evident upon multiple administration of the non-human antibody to a human patient. Various techniques have been developed over the years to overcome these problems and generally involve reducing the composition of non-human amino acid sequences in the intact antibody whilst retaining the relative ease in obtaining non-human antibodies from an immunised animal, e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention, e.g. DNA encoding SEQ ID NO 1, 2, 3, 4, 5 and 6 described supra). Hybridoma cells serve as a typical source of such DNA. Once isolated, the DNA is placed into expression vectors which are then transfected into host cells such as E.Coli, COS cells, CHO cells or myeloma cells that do not otherwise produce immunoglobulin protein to obtain synthesis of the antibody. The DNA may be modified by substituting the coding sequence for human L and H chains for the corresponding non. human (e.g. murine) H and L constant regions see e.g. Morrison; PNAS 81, 6851 (1984).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework region. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ('donor' antibodies) onto human framework ('acceptor framework') and constant regions (see Jones et al (1986) Nature 321, 522-525 and Verhoeyen M et al (1988) Science 239, 1534-1536). However, CDR grafting per se may not result in the complete retention of antigen-binding properties and it is frequency found that some framework residues (sometimes referred to as 'backmutations') of the donor antibody need to be preserved in the humanised compound if significant antigen-binding affinity is to be recovered (see Queen C et al (1989) PNAS 86, 10, 029-10,033, Co, Met al (1991) Nature 351, 501-502). In this case, human V regions showing the greatest sequence homology to the non-human donor antibody are chosen from a database in order to provide the human framework (FR). The selection of human FRs can be made either from human consensus or individual human antibodies. Where necessary key residues from the donor artibody are substituted into the human acceptor framework to preserve CDR conformations. Computer modelling of the antibody may be used to help identify such structurally important residues, see WO99/48523.

Alternatively, humanisation may be achieved by a process of 'veneering'. A statistical analysis of unique human and murine immunoglobulin heavy and light chain variable regions revealed that the precise patterns of exposed residues are different in human and murine antibodies, and most individual surface positions have a strong preference for a small number of different residues (see Padlan E A, et al; (1991) Mol Immunol 28, 489-498 and Pedersen if et al (1994) J Mol Biol 235; 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region 'invisible' to the human immune system (see also Mark G E et al (1994) in Handbook of Experimental Pharmacology vol 113: The pharmacology of monoclonal Antibodies, Springer-Verlag, pp 105-134). This procedure of humanisation is referred to as 'veneering' because only the surface of the antibody is altered, the supporting residues remain undisturbed.

Thus in one embodiment of the invention there is provided an intact therapeutic humanised antibody capable of binding NRG1 (e.g. NRG1β1) and neutralizing the biological activity thereof. In particular the intact therapeutic humanised antibody binds with NRG1β1 and inhibits the interaction between NRG1β1 and its cognate receptor ErbB2 and/or ErbB3. In typical embodiments the intact therapeutic humanised antibody comprises a constant region of an IgG isotype, e.g. IgG1 or IgG4.

In another embodiment, there is provided an intact therapeutic humanised antibody capable of preferentially binding NRG1β1 (compared with NRG1a) and neutralizing the biological activity thereof. In particular the intact therapeutic humanised antibody preferentially binds with NRG1β1 and inhibits the interaction between NRG1β1 and its cognate receptor ErbB2 and/or ErbB3. In preferred forms, the intact therapeutic human antibody comprises a constant region of an IgG isotype, e.g. IgG1 or IgG4.

In another embodiment, there is provided an intact therapeutic humanised antibody capable of specifically binding NRG1β1 (compared with NRG1a) and neutralizing the biological activity thereof. In particular the intact therapeutic humanised antibody specifically binds with NRG1β1 and inhibits the interaction between NRG1 and its cognate receptor ErbB2 and/or ErbB3. In preferred forms, the intact therapeutic humanised antibody comprises a primate, and in particular a human constant region of an IgG isotype, e.g. IgG1 or IgG4.

4.1.1.1.3 Bispecific Antibodies

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities, (see Millstein et al, Nature 305, 537-539 (1983), WO93/08829 and Traunecker et al, EMBO, 10, 1991, 3655-3659). Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions and, if desired, the L chain are inserted into separate expression vectors and are the contransfected into a suitable host organism. It is possible though to insert the coding sequences for two or all three chains into one expression vector. In one preferred approach, the bispecific antibody is composed of an H chain with a first binding specificity in one arm and an H-L chain pair, providing a second binding specificity in the other arm, see WO94/04690. Also see Suresh et al, Methods in Enzymology 121, 210, 1986.

In one embodiment of the invention there is provided a bispecific therapeutic antibody wherein at least one binding specificity of said antibody is for NRG1, particularly NRG1β1, wherein said antibody binds with and neutralises NRG1 (e.g. NRG1β1) biological activity. In preferred forms the bispecific antibody comprises a primate, e.g. human antibody of a IgG (e.g. IgG1 or IgG4) isotype.

4.1.1.1.4 Antibody Fragments

In certain embodiments of the invention there is provided therapeutic antibody fragments which modulate (e.g. inhibit) the interaction between NRG1 and its cognate receptor e.g. ErbB2 and/or ErbB3 for example ErbB2/ErbB3 heterodimer. Such fragments may be functional antigen binding fragments of intact and/or humanised chimaeric antibodies such as Fab, Fab', F(ab')$_2$, Fv, ScFv fragments of the antibodies described supra.

Traditionally, such fragments are produced by the proteolytic digestion of intact antibodies by e.g. papain digestion (see for example WO 94/29348) but may be produced directly from recombinantly transformed host cells. For the production of ScFv, see Bird et al; (1988) Science, 242, 423-426. In addition, antibody fragments may be produced using a variety of engineering techniques as described below.

FV fragments appear to have lower interaction energy of their two chains than Fab fragments. To stabilise the association of the VH and VL domains, they have been linked with peptides (Bird et al, (1988) Science, 242, 423-426, Huston et al, PNAS, 85, 5879-5883), disulphide bridges (Glockshuber et al, (1990) Biochemistry, 29, 1362-1367) and 'knob in hole' mutations (Zhu et al (1997), Protein Sci., 6, 781-788). ScFv fragments can be produced by methods well known to those skilled in the art (see Whitlow et al (1991), Methods companion Methods Enzymol, 2, 97-105 and Huston et al (1993) Int Rev Immunol 10, 195-217. ScFv may be produced in bacterial cells such as *E.Coli* but are more preferably produced in eukaryotic cells. Om disadvantage of ScFv is the monovalency of the product, which precludes an increased avidity due to polyvalent binding, and their short half-life. Attempts to overcome these problems include bivalent (ScFv')$_2$ produced from ScFv containing an additional C terminal cysteine by chemical coupling (Adams et al (1993) Can Res 53, 4026-4034 and McCartney et al (1995) Protein Eng, 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to 3 and 12 residues to form 'diabodies' (see Holliger et al PNAS (1993), 90, 6444-6448). Reducing the linker still further can result in ScFV trimers ('triabodies', see Kortt et al (1997) Protein Eng, 10, 423-433) and tetramers ('tetrabodies', see Le Gall et al (1999) FEBS Lett, 453, 164-168). Construction of bialent ScFV compounds can also be achieved by genetic fusion with protein dimerzing motifs to form 'miniantibodies' (see Pack et al (1992) Biochemistry 31, 1579-1584) and 'minibodies' (see Hu et al (1996), Cancer Res. 56, 3055-3061). ScFv-Sc-Fv tandems ((ScFV)2) may also be produced by linking two ScFV units by a third peptide linger, (see Kurucz et al (1995) J Immunol, 154, 4576-4582). Bispecific diabodies can be produced through the noncovalent association of two single chain fusion products consisting of VH domain from one antibody connected by a short linker to the VL domain of another antibody, (see Kipriyanov et al (1998), Int J Can 77, 763-772). The stability of such bispecific diabodies can be enhanced by the introduction of disulphide bridges or 'knob in hole' mutations as described supra or by the formation of single chain diabodies (ScDb) wherein two hydrid ScFv fragments are connected through a peptide linker (see Kontermann et al (1999) J Immunol Methods 226, 179-188). Tetravalent bispecific compounds are available by e.g fusing a ScFv fragment to the CH3 domain of an IgG compound or to a Fab fragment through the hinge region (see Coloma et al (1997) Nature Biotechnol, 15, 159-163). Alternatively, tetravalent bispecific compounds have been created by the fusion of bispecific single chain diabodies (see Alt et al (1999) FEBS Lett 454, 90-94). Smaller tetravalent bispecific compounds can also be formed by the dimerization of either ScFv-ScFv tandems with a linker containing a helix-loop-helix motif (DiBi miniantibodies, see Muller et al (1998) FEBS Lett 432, 45-49) or a single chain compound comprising four antibody variable domains (VH and VL) in an orientation preventing intramolecular pairing (tandem diabody, see Kipriyanov et al, (1999) J Mol Biol 293, 41-56). Bispecific F9ab')$_2$ fragments can be created by chemical coupling of Fab' fragments or by heterodimerization through leucine zippers (see Shalaby et al (1992) J Exp Med 175, 217-225 and Kostelny et al (1992), J Immunol 148 1547-1553). Also available are isolated VH and VL domains (Domantis plc), see U.S. Pat. No. 6,248,516; U.S. Pat. No. 6,291,158; U.S. Pat. No. 6,172,197 and isolated VHH domain antibodies (Nanobodies). These domain and nanobodies may be dual specific having one specificity directed to a half life extending protein such as human serum albumin (HSA). Such domain and nanobodies both monospecific for a NRG1 protein of the invention and further dual specific for a half life extending protein such as HSA are specifically contemplated by the invention.

In one embodiment there is provided a therapeutic antibody fragment (e.g. ScFv, Fab, Fab', F(ab')$_2$) or an engineered antibody fragment as described supra that binds (e.g. preferentially or specifically binds) with NRG1, e.g. NRG1β1 and neutralises the biological activity thereof by e.g. inhibiting the interaction between NRG1 and its cognate receptor e.g. ErbB2 and/or ErbB3, for example ErbB2/ErbB3 heterodimer.

4.1.1.1.5 Heteroconjugate Antibodies

Heteroconjugate antibodies also form an embodiment of the present invention.

Heteroconjugate antibodies are composed of two covalently joined antibodies formed using any convenient cross-linking methods. See, for example, U.S. Pat. No. 4,676,980.

4.1.1.1.6 Other Modifications

The interaction between the Fc region of an antibody and various Fc receptors (FcγR) is believed to mediate the effector functions of the antibody which include antibody-dependent cellular cytotoxicity (ADCC), fixation of complement, phagocytosis, and half-life/clearance of the antibody. Various modifications to the Fc region of antibodies of the invention may be carried out depending on the desired property. For example, specific mutations in the Fc region to render an otherwise lytic antibody, non-lytic is detailed in EP 0629 240B 1 and Ep 0307 434B2 or one may incorporate a salvage receptor binding epitope into the antibody to increase serum half- life, see U.S. Pat. No. 5,739,277. There are five currently recognised human Fcγ, FcγR (I), FCγRIIb, FcγRIIIa and neonatal FcRn. Shields et al, (2001) J Biol Chem 276, 6591-6604 demonstrated that a common set of IgG1 residues is involved in binding all FcγRs, while FCγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected).

Other variants exhibited improved binding to DcγRII or FcγRIII with reduction in binding to the other receptor (e.g. Ser298Ala improved binding to FcγRIII and reduced binding to FcγRII). For FcγRIIIa, the best binding IgG1 variants had combined alanine substitutions at Ser-298, Glu-333 and Ls-334. The neonatal FcRn receptor is believed to be involved in both antibody clearance and the transcytosis across tissues (see Junghans R P (1997) Immunol Res 16, 2957 and Ghetie et al (2000) Annu Rev Immunol 18, 739-766). Human IgG1 residues determined to interact directly with human FcRn included Ile253, Ser254, Lys288, Thr307, Gln311, Asn434 and His435. Switches at any of these positions described in this section may enable increased serum half-life and/or altered effector properties of antibodies of the invention and therefore forms an embodiment of the invention.

Other modifications include glycosylation variants of the antibodies of the invention. Glycosylation of antibodies at conserved positions in their constant regions is known to have a profound effect on antibody function, particularly effector functioning such as those described above, see for example, Boyd et al (1996), Mol Immmol 32, 1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serin or asparagine-X-threonine motif creates a potential side for enzymatic attachment of carbonhydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactrosyltransferace and/or alpha, 2, 3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al, Science (2004), 303, 371; Sears et al, Science (2001), 291, 2344; Wacker et al (2002), Science 298, 1790; Davis et al (2002), Chem Rev 102, 579; Hang et al (2001), Acc Chem Res 34, 727. Thus the invention contemplates a plurity of therapeutic (monoclonal) antibodies (which may be of the IgG isotype, e,g. IgG1) as herein described comprising a defined number (e.g. 7 or less, for example 5 or less such as two or a single) glycoform(s) or said antibodies or antigen binding fragments thereof.

Further embodiments of the invention include therapeutic antibodies of the invention or antigen binding fragments thereof coupled to a non0proteinaeous polymer such as polyethylene glycol (PEG), polypropylene glycol or polyoxyalkylene. Conjugation of proteins to PEG is an established technique for increasing half- life of proteins, as well as reducing antigenicity and immunogenicity of proteins. The use of PEGylation with different molecular weights and styles (linear or branched) has been investigated with intact antibodies as well as Fab' fragments (see Koumenis IL et al (2000) Int J Pharmaceut 198;83-95.

4.2 Adnectins—Compound Therapeutics

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based compounds can be used as scaffolds where the loop regions of the compound can be replaced with CDRs of the invention using standard cloning techniques. Accordingly, in some embodiments there is provided an adnectin compound that binds with and neutralises the biological activity of NRG1 and in particular NRG1β1.

4.3 Ankyrin—Molecular Partners

This technology is based on using proteins with ankyrin derived repeat modules as scaffolds for bearing variable regions which can be used for binding to different targets. The ankyrin repeat module is a 33 amino acid polypeptide consisting of two anti-parallel a-helices and a β-turn. Binding of the variable regions is mostly optimized by using ribosome display. Accordingly, in some embodiments there is provided an Ankyrin compound that binds with and neutralises the biological activity of NRG1 and in particular NRG1β1.

4.4 Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US20040175756; US20050053973; US20050048512; and US20060008844. Accordingly, in some embodiments there is provided an Maxybody compound that binds with and neutralises the biological activity of NRG1 and in particular NRG1β1.

4.5 Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® compounds mimic antibodies, they have a molecular weight of 6 kDa, compared to the molecular weight of antibodies, which is 150 kDa. In spite of its small size, the binding site of Affibody® compounds is similar to that of an antibody. Accordingly, in some embodiments there is provided an Protein A-affibody compound that binds with and neutralises the biological activity of NRG1 and in particular NRG1β1.

4.6 Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compound s. Several natural lipocal ins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target compounds of different shape with high affinity and specificity.

One protein of lipocalin family, the bilin-binding protein (BBP) of Pieris

Brassicae has been used to develop anticalins by mutagenizing the set of four loops. One example of a patent application describing "anticalins" is PCT WO 199916873.

Accordingly, in some embodiments there is provided an anticalin compound that binds with and neutralises the biological activity of NRG1 and in particular NRG1β1.

4.7 Affilin—Scil Proteins

Affilin™ compounds are small non-immunoglobulin proteins which are designed for specific affinities towards proteins and small compounds. New Affilin™ compounds can be very quickly selected from two libraries, each of which is based on a different human derived scaffold protein. Affilin™ compounds do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368. Accordingly, in some embodiments there is provided an Affilin compound that binds with and neutralises the biological activity of NRG1 and in particular NRG1β1.

4.7.1—Other Therapeutic Modalities

As noted previously, other therapeutic modalities of this invention include modulators (particularly inhibitors) of NRG1, and in particular NRG1β1 which exert their effect on their target prior to protein expression. Examples include anti-sense oligonucleotides that comprise (or consist essentially of) a sequence (a) capable of forming a stable triplex with a portion of the NRG1 (particularly NRG1β1) gene, or (b) capable of forming a stable duplex with a portion of an mRNA transcript of the NRG1 (particularly NRG1β1) gene under physiological conditions. Other examples include molecules that can participate in the phenomena of "RNA interference". RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof Conveniently, the dsRNA can be produced from a single promoter in a recombinant vector or host cell, where the sense and anti-sense sequences are flanked by an unrelated sequence which enables the sense and anti-sense sequences to hybridise to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated.

The DNA therefore comprises both sense and antisense sequences that, when transcribed into RNA, can hybridise to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous mammalian system that destroys both the double stranded RNA and also the homologous RNA transcript from the target mammalian gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilise the molecule. The RNA molecule may be expressed under the control of a RNA polymerase II or RNA polymerase HI promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search. MicroRNA regulation is a clearly specialised branch of the RNA silencing pathway that evolved towards gene regulation, diverging from conventional RNAi/PTGS.

MicroRNAs are a specific class of small RNAs that are encoded in gene-like elements organised in a characteristic inverted repeat. When transcribed, microRNA genes give rise to stem-looped precursor RNAs from which the microRNAs are subsequently processed. MicroRNAs are typically about 2 1 nucleotides in length. The released miRNAs are incorporated into RISC-like complexes containing a particular subset of Argonaute proteins that exert sequence-specific gene repression (see, for example, Millar and Waterhouse, 2005; Pasquinelli et al. 2005; Almeida and Allshire, 2005).

4.8 Production Methods

Therapeutic proteins of the invention, and particularly antibodies maybe produced as a polyclonal population but are more preferably produced as a monoclonal population (that is as a substantially homogenous population of identical antibodies directed against a specific antigenic binding site). It will of course be apparent to those skilled in the art that a population implies more than one antibody entity. Antibodies of the present invention may be produced in transgenic organisms such as goats (see Pollock et al (1999), J. Immunol. Methods 231 :147-157), chickens (see Morrow K J J (2000) Genet. Eng. News 20:1- 55, mice (see Pollock et al) or plants (see Doran P M, (2000) Curr.Opinion Biotechnol. 11 , 199-204, Ma JK-C (1998), Nat. Med. 4; 601-606, Baez J e. al, BioPharm (2000) 13: 50-54, Stoger E et al; (2000) Plant Mol. Biol. 42:583-590). Antibodies may also be produced by chemical synthesis. However, antibodies and other therapeutic proteins of the invention are typically produced using recombinant cell culturing technology well known to those skilled in the art. A polynucleotide encoding the antibody is isolated and inserted into a replicable vector such as a plasmid for further cloning (amplification) or expression. One useful expression system is a glutamate synthetase system (such as sold by Lonza Biologies), particularly where the host cell is CHO or NSO (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and transfected into the same host cell or, if desired both the heavy chain and light chain can be inserted into the same vector for transfection into the host cell. Thus according to one aspect of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention.

4.8.1 Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, [alpha] factor leader or acid phosphatase leaders see e.g. WO90/13646. In mammalian cell systems, viral secretory leaders such as herpes simplex gD signal and a native immunoglobulin signal sequence are available. Typically the signal sequence is ligated in reading frame to DNA encoding the antibody of the invention.

4.8.2 Origin of Replication

Origin of replications are well known in the art with pBR322 suitable for most gram-negative bacteria, 2µ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

4.8.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. In typical embodiments, cells are cultured in the presence of increasing amounts of methotrexate to amplify the copy number of the exogenous gene of interest. CHO cells are a particularly useful cell line for the DHFR selection. A further example is the glutamate synthetase expression system (Lonza Biologies). A suitable selection gene for use in yeast is the trp1 gene, see Stinchcomb et al Nature 282, 38, 1979.

4.8.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression.

4.8.5 Enhancer Element

Where appropriate, e.g. for expression in higher eukaroytics, an enhancer element operably linked to the promoter element in a vector may be used. Suitable mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine lgG2a locus (see WO04/009823). The enhancer is preferably located on the vector at a site upstream to the promoter.

4.8.6 Host Cells

Suitable host cells for cloning or expressing vectors encoding antibodies of the invention are prokaroytic, yeast or higher eukaryotic cells. Suitable prokaryotic cells include eubacteria e.g. enterobacteriaceae such as *Escherichia* e.g. *E.Coli* (for example ATCC 31, 446; 31, 537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B.subtilis* and *B.licheniformis* (see DD 266 710), *Pseudomonas* such as *P.aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183, 070, see also Peng et al J. Biotechnol. 108 (2004) 185-192), *Candida, Thchoderma reesia* (EP244, 234J, *Penicillin, Tolypocladium* and *Aspergillus* hosts such as *A.nidulans* and *A.niger* are also contemplated.

Although Prokaryotic and yeast host cells are specifically contemplated by the invention, preferably however, host cells of the present invention are higher eukaryotic cells. Suitable higher eukaryotic host cells include mammalian cells such as COS-1 (ATCC No.CRL 1650) COS-7 (ATCC CRL 1651), human embryonic kidney line 293, baby hamster kidney cells (BHK) (ATCC CRL.1632), BHK570 (ATCC NO: CRL 10314), 293 (ATCC NO.CRL 1573), Chinese hamster ovary cells CHO (e.g. CHO-K1, ATCC NO: CCL 61, DHFR: CHO cell line such as DG44 (see Urlaub et al, (1986) Somatic Cell Mol .Genet.12, 555-556)), particularly those CHO cell lines adapted for suspension culture, mouse Sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NSO (see U.S. Pat. No. 5,807,715), Sp2/0, YO. Thus in one embodiment of the invention there is provided a stably transformed host cell comprising a vector encoding a heavy chain and/or light chain of the therapeutic antibody or antigen binding fragment thereof as herein described. Preferably such host cells comprise a first vector encoding the light chain and a second vector encoding said heavy chain.

4.6.1 Bacterial Fermentation

Bacterial systems may be used for the expression of non-immunoglobulin therapeutic proteins described above. Bacterial systems are also particularly suited for the expression of antibody fragments. Such fragments are localised intracellular or within the periplasma. Insoluble periplasmic proteins can be extracted and refolded to form active proteins according to methods known to those skilled in the art, see Sanchez et al (1999) J. Biotechnol. 72, 13-20 and Cu pit PM et al (1999) Lett Appl Microbiol, 29, 273-277.

4.8.7 Cell Culturing Methods.

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Preferably the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such as fetal calf serum (FCS), it is preferred that such host cells are cultured in synthetic serum -free media such as disclosed in Keen et al (1995) Cytotechnology 17:153-163, or commercially available media such as ProCHO-CDM or UltraCHO (TM) (Cambrex N.J., USA), supplemented where necessary with an energy source such as glucose and synthetic growth factors such as recombinant insulin. The serum- free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K a al (1995) in Animal Cell technology: Developments towards the 21st century (Beuvery E. G. et al eds), pp 619-623, Kluwer Academic publishers).

Antibodies or other therapeutic proteins of the invention secreted into the media may be recovered and purified using a variety of techniques to provide a degree of purification suitable for the intended use. For example the use of therapeutic antibodies of the invention for the treatment of human patients typically mandates at least 95% purity, more typically 98% or 99% or greater purity (compared to the crude culture medium). In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429, 746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (preferably monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

4.9—Screening Methods

In other embodiments, there are provided methods of identifying modulators (such as antagonists) capable of modulating the interaction between NRG1 (e.g. NRG1β1) and its cognate receptor or receptors (e.g. ErbB2/ErbB3 heterodimer). In some embodiments, the modulator neutralizes the biological activity of NRG1.

In accordance therefore with the present invention there is provided a method of screening a candidate compound for its ability to neutralize the biological activity of NRG1 (particularly NRG 1β1) by e.g. inhibiting the interaction between NRG1 (e.g. NRG1β1) and a cognate receptor such as ErbB2/ErbB3 heterodimer which method comprises contacting said NRG1 (e.g. NRG1β1) with said candidate compound (e.g a candidate antibody) and detecting a modulation in the interaction between said NRG1 and one or both of its cognate receptors.

In accordance therefore with the present invention there is provided a method for screening a candidate compound for its ability to modulate (e.g. inhibit) the interaction between NRG1 (e.g. NRG1β1) and a cognate receptor (e.g. ErbB2/ErbB3 heterodimer) which method comprises contacting said NRG1 (e.g. NRG1β1) with said candidate compound (e.g. a candidate antibody) and detecting neutralization of the biological activity of NRG1β1.

In one embodiment, the method comprises detecting a change in MUC5AC and/or MUC5B expression on a cell capable of expressing MUC5AC and/or MUC5B. An example of such a cell is an epithelial cell such as a goblet cell. Methods for detecting changes to such expression will be apparent to the skilled person. Thus in one embodiment of the invention there is provided a method for screening a candidate inhibitor of the interaction between NRG1 (e.g. NRG1β1) and a cognate receptor (such as a ErbB2 and/or ErbB3) which method comprises contacting said NRG 1 with said candidate compound in the presence of a cell expressing MUC5AC and/or MUC5B and detecting a change (e.g. reduction) in expression of MUC5AC and/or MUC5B compared to the expression of said MUC5AC and/or MUC5B on said cell in the presence of said NRG1 without said candidate compound.

In another embodiment, the method comprises detecting a change in goblet cell hyperplasia in the presence of said candidate compound. Thus in one aspect of the invention there is provided a method of/for screening a candidate inhibitor of the interaction between NRG1 (e.g. NRG1β1) and a cognate receptor (such as a ErbB2 and/or ErbB3, e.g. ErbB2/ErbB3 heterodimer) which method comprises contacting said NRG 1 with said candidate compound in the presence of a goblet cell and detecting a change (e.g. reduction) in goblet cell division compared to goblet cell division in the absence of said candidate compound.

4.10 Pharmaceutical Compositions

The invention provides pharmaceutical compositions comprising the therapeutic protein or low molecular weight chemical entity formulated together with a pharmaceutically acceptable carrier. The compositions can additionally contain other therapeutic agents that are suitable for treating or preventing a human disease or disorder noted below. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound (particularly low molecular weight chemical entities) may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the modulator of NRG1 (e.g. NRG1β1) such as a NRG1β1 antibody described herein is employed in the pharmaceutical compositions of the invention. They are typically formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic.

Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody and other protein therapeutics are usually administered on multiple occasions. Intervals between single dosages can be weekly, monthly or yearly.

Intervals can also be irregular as indicated by measuring blood levels of therapeutic protein in the patient. In some methods, dosage is adjusted to achieve a plasma antibody concentration of 1-1000 μg/ml and in some methods 25-300 μg/ml. Alternatively, antibody or other protein therapeutics can be administered as a sustained release formulation, in which case less frequent administration is required. Dosage and frequency vary depending on the half- life of the antibody or other protein therapeutic in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

4.11 Clinical Uses

The present invention is based, at least in part on the finding that members of the neuregulin family (particularly the NRG1 family e.g. NRG1β and in particular NRG1β1) promote goblet cell formation. Therefore modulators (particularly antagonists) of the present invention may be useful in the treatment of human diseases or disorders in which aberrant goblet cell formation plays a pathological role. In accordance therefore the present invention provides a method of treating a disease or disorder of goblet cell cycle regulation which method comprises administering to a human patient in clinical need thereof a therapeutically effective amount of a modulator of NRG1 biological activity. In some embodiments, the modulator is an antagonist (such as an antibody, particularly a human or humanized antibody of an IgG isotype or an antibody fragment thereof) which binds with either NRG1 (e.g. NRG1β1) and/or a cognate receptor thereof (such as ErbB2 and/or ErbB3, particularly ErbB2/ErbB3 heterodimer) and inhibits the interaction there between. In other embodiments there is provided a method of treating a disease or disorder of goblet cell cycle regulation (for example goblet cell hyperplasia) comprising administering to a human patient in clinical need thereof a therapeutically effective amount of a therapeutic protein that binds with NRG1β1 (such as a human or humanized antibody of an IgG1 or IgG4 isotype as herein described which preferentially or specifically binds with NRG1β1). Examples of clinical diseases or disorders in which goblet cell hyperplasia contributes include respiratory diseases such as chronic obstructive pulmonary disease (COPD), cystic fibrosis (CF), chronic bronchitis, asthma (particularly moderate and severe forms thereof).

Therefore in some embodiments there is provided a method of treating a human patient afflicted with a respiratory disease such as COPD, CF, chronic bronchitis or asthma (particularly moderate to severe forms thereof) which method comprises administering to said patient a therapeutically effective amount of a modulator of NRG1 (e.g. NRG1β1) biological activity. In preferred forms of these embodiments, the modulator is an antibody (particularly a human or humanized antibody of an IgG1 or IgG4 isotype or an antibody fragment that binds with (e.g. preferentially or specifically binds with) NRG1 (particularly NRG1β1) and neutralizes the biological activity of NRG1, particularly NRG1β1. In this regard, "biological activity" as used throughout this specification in reference to NRG 1 and in particular NRG 1β1 refers to the activity of these proteins in promoting the expression of MUC5AC and/or MUC5B. Thus "neutralizes the biological activity" and the like as used throughout this specification refers to the inhibition of MUC5B and/or MUC5AC expression by a modulator of the invention.

In some embodiments, there is provided a method of treating a human patient afflicted with a disease or disorder comprising aberrant mucus production such as COPD, CF, chronic bronchitis or asthma (particularly the severe or moderate forms thereof) or a disease or disorder of the lower respiratory tract (e.g. an infection of the lower respiratory tract) which method comprises administering to said patient a therapeutically effective amount of an inhibitor (for example a human or humanized antibody of a IgG1 or IgG4 isotype) of the interaction between NRG1 (particularly NRG1β1) and one or more of its cognate receptors (e.g. ErbB2 and/or ErbB3, particularly ErbB2/ErbB3 heterodimer). In preferred forms of these embodiments, the modulator is a human or humanized antibody or antibody fragment as described herein which preferentially or more preferably specifically binds with NRG1β1 and inhibits said aberrant mucus secretion.

In some embodiments, there is provided a method of treating a human patient afflicted with a respiratory disease or disorder as COPD, CF, bronchitis (particularly chronic bronchitis) or asthma (particularly the severe or moderate forms thereof) or a disease or disorder of the lower respiratory tract (e.g. an infection of the lower respiratory tract), pneumonia, emphysema which method comprises administering to said patient a therapeutically effective amount of an inhibitor (for example a human or humanized antibody of a IgG1 or IgG4 isotype) of the interaction between NRG1 (particularly NRG1β1) and one or more of its cognate receptors (e.g. ERB2 and/or ERB3, particularly "ErbB"2/ErbB3 heterodimer).

In some embodiments, there is provided a method of treating the aberrant mucus production aspect of a respiratory disease such as COPD, CF, chronic bronchitis or asthma (particularly severe or moderate forms thereof) which method comprises administering to said human patient a therapeutically effective amount of a modulator (such as a human or humanized antibody) which neutralizes the biological activity of NRG1, and in particular NRG1β1.

In other embodiments there is provided a method of treating prophylactically a human patient at risk of being afflicted with a respiratory disease or disorder characterized by aberrant mucus production (such as COPD, chronic bronchitis, cystic fibrosis, asthma) which method comprises administering to said patient a therapeutically effective amount of a modulator (such as therapeutic protein e.g. a human or humanized antibody of a IgG isotype e.g. IgG1 or IgG4 as herein described) which modulates the interaction between a NRG1 (particularly NRG1β and more particularly NRG1β1) and one or more of its cognate receptor (e.g. ErbB2 and/or ErbB3). In some embodiments, the modulator neutralizes the biological activity of NRG1.

In other embodiments of the invention there is provided a method of treating a human patient afflicted with a respiratory disease or disorder such as COPD, CF, chronic bronchitis which method comprises co-administering an inhibitor (such as a therapeutic protein e.g. a human or humanized antibody as described herein) of NRG1 (particularly NRG1β and more particularly NRG1β1) biological activity together with an anti-human IL-13 agent (such as an IL-13 antibody, particularly a human or humanized IL-13 antibody) and/or with an anti-human IL-4 agent (such as an IL-4 antibody, particularly a human or humanized IL-4 antibody) and/or with an anti-human IL-5 agent (such as an IL-5 antibody, particularly a human or humanized IL-5 antibody) and/or an anti-IgE agent (such as a human or humanized anti-IgE antibody and/or anti-IL-17 (particularly IL-17A) antibody (such as a human or humanized anti-IL-17, e.g. IL-17A antibody). Each of these combinations is specifically and separately contemplated.

Although the present invention has been described principally in relation to the treatment of human diseases or disorders, the skilled person will readily appreciate that the teaching herein may be applied to the treatment of similar diseases or disorders in non human mammals.

5. EXEMPLIFICATIONS

The present invention is now described by way of example only.

5.1 Brief Description of the Figures

FIG. 1. Effect of NRG1 beta1 and NRG1 alpha on MUC5AC expression

Human Bronchial Epithelial Cells (HBECs) were treated with increasing concentrations of NRG1β1 (A) or NRG1α (B) for 7 days and stained with an anti-MUC5AC (45M1) monoclonal antibody. The proportion of MUC5AC positive cells was assessed by image analysis. (C) Representative histology images the MUC5AC/alcian blue stained vehicle and NRG1β1 (50 nM) treated HBECs. The arrow indicates an alcian blue stained cell which does not stain with the anti-MUC5AC antibody. The results shown are representative results from experiments on 3 independent donors. The results shown are the mean±SEM (n=3). Significant differences from the untreated control are indicated ($*P<0.05$).

Figure 2:
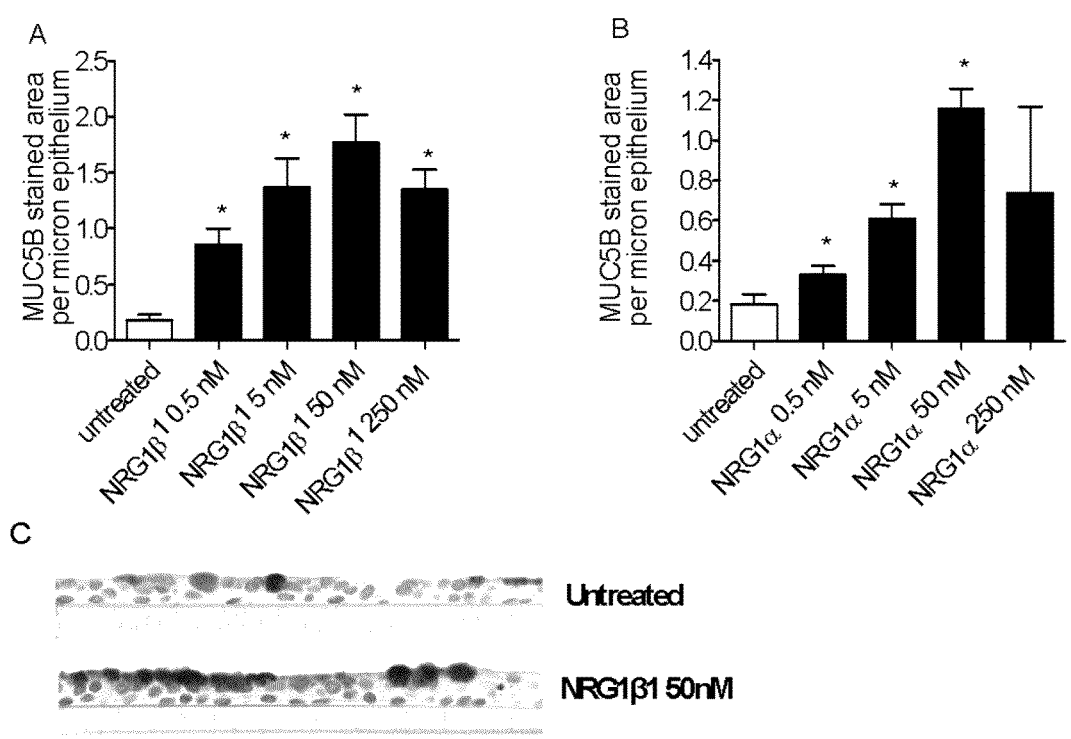

FIG. 2: Effect NRG1 alpha and beta1 on MUC5B protein

The effects of increasing concentrations of NRG1β1 (A) and NRG1a (B) on MUC5B protein, as assessed by immunohistochemistry. Cells were treated with NRG1 for 7 days. (C) Representative histology images the MUC5B/alcian blue stained vehicle and NRG1β1 (50 nM) treated HBECs. The results shown are the mean±SEM (n=3). Significant differences from the untreated control are indicated ($*P<0.05$).

Figure 3:
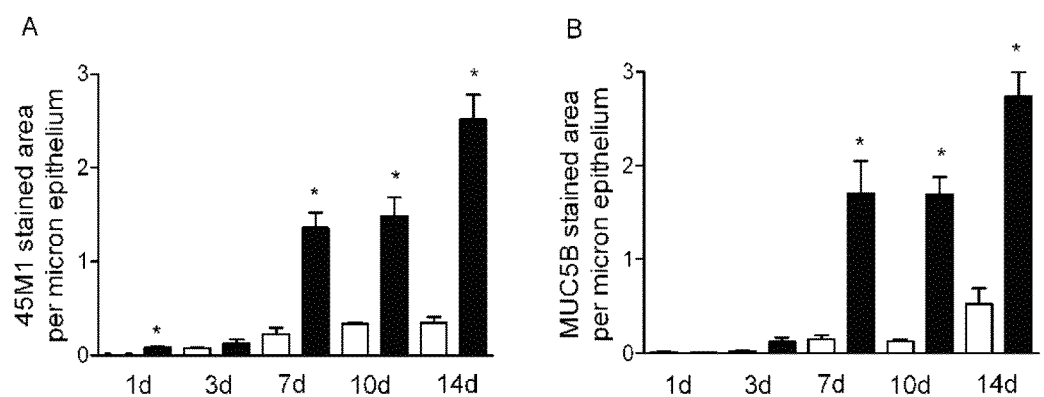

FIG. 3: Effects of NRG1 beta1 on MUC5AC and MUC5B expression over a time course

The effects of NRG1β1 (50 nM) on MUC5AC protein (A) and MUC5B protein (B) over 1 to 14 days treatment as assessed by histology. NRG1β1 treated samples are shown in black and untreated samples in white. The results shown are the mean±SEM (n=3). Significant differences from the untreated control are indicated ($*P<0.05$).

Figure 4:
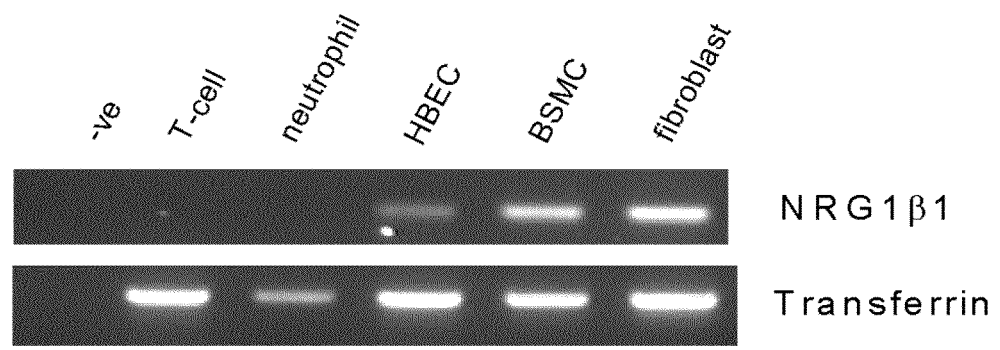

FIG. 4: NRG1 beta1 expression in primary cells

NRG1β1 expression was analysed by RT-PCR in a panel of primary cells which included T-cells, Neutrophils, Human Bronchial Epithelial Cells (HBECs) Bronchial Smooth Muscle Cells (BSMCs) and lung fibroblasts. The expression of the housekeeping gene transferrin was also analysed. Data is representative of data obtained with cells from at least 2 independent donors.

Figure 5:
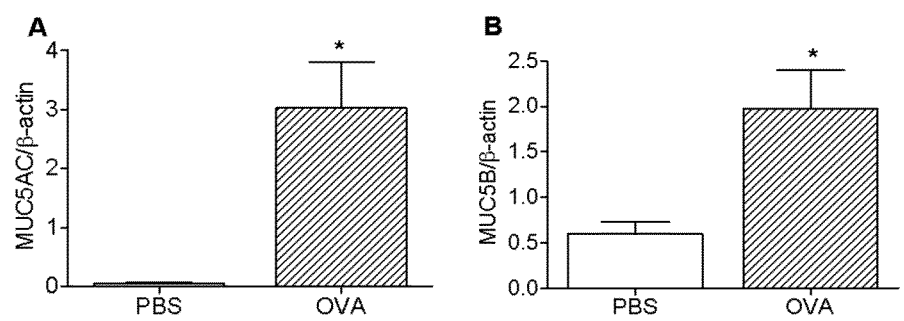

FIG. 5: MUC5AC and MUC5B expression in lungs of ovalbumin challenged mice

Expression of MUC5AC (A) and MUC5B (B) was analysed by quantitative RT-PCR in lung tissue from OVA challenged Balb/c mice. Data is shown as mean±SEM (n=8 per group) and is shown normalised to the housekeeping gene β-actin. $*p<0.05$ compared to saline challenged mice.

Figure 6:
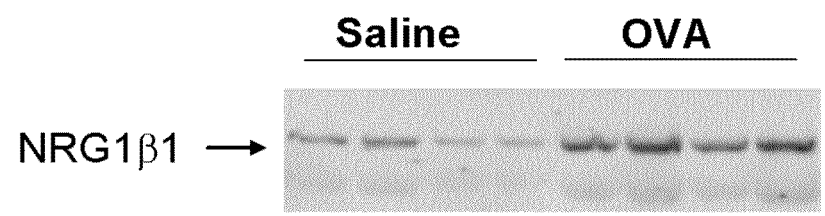

FIG. 6: Western blot analysis of NRG1 beta1 protein in BAL fluid from OVA challenged mice BAL fluid from OVA challenged mice was analysed for NRG1β1 protein by western blot. Blots were probed with an antibody (sc-347) which recognizes preferentially the NRG1β1 isoform. BAL fluid from 4 animals was analysed for each treatment. Data shown are representative of data obtained with 2 independent sets of samples.

Figure 7:
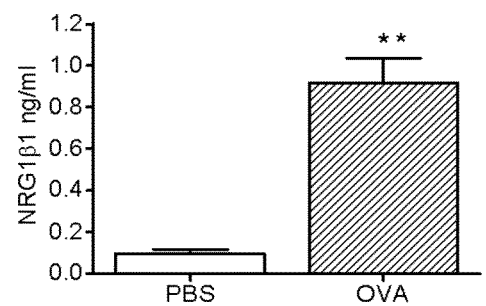

FIG. 7: NRG1 beta1 ELISA

NRG1β1 protein was quantified in BAL fluid from OVA challenged mice. Data is shown as mean±SEM (n=4 mice per group). The data shown is representative of 2 independent sets of samples. $**p<0.001$ compared to saline challenged mice.

Figure 8:
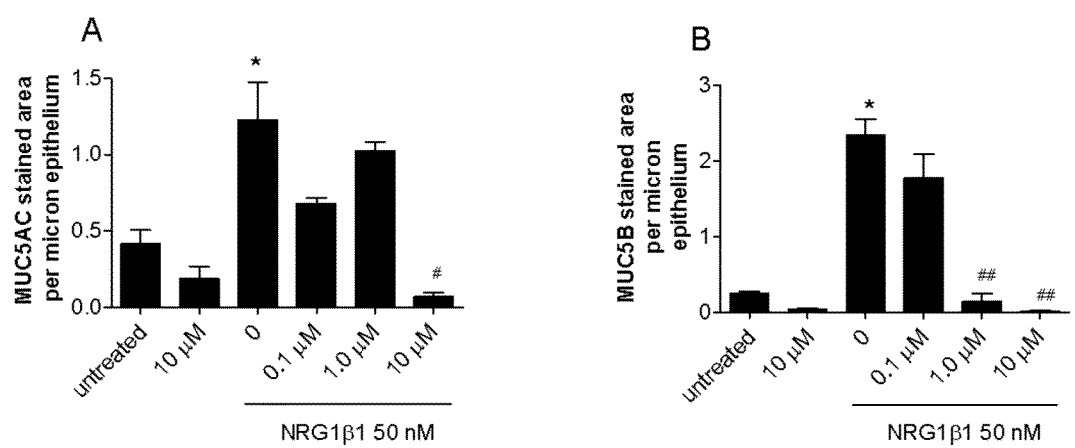

FIG. 8: Effects of a pan-ErbB receptor inhibitor on goblet cell formation.

The effects of a pan-ErbB receptor inhibitor on NRG1β1-induced goblet cell formation are shown. The effects of inhibitor (1-10 μM) on NRG1β1-induced MUC5AC (A) and MUC5B (B) protein were determined by histology. Cells were either untreated or treated with NRG1β1 (50 nM) as indicated. * Significant difference from the untreated control ($P<0.05$); # significant difference from the NRG1β1 only treated group ($P<0.05$); ## significant difference from the NRG1β1 only treated group ($P<0.001$). The results are shown as the mean ±2SEM (n=3) and are representative of 2 independent experiments.

Figure 9:
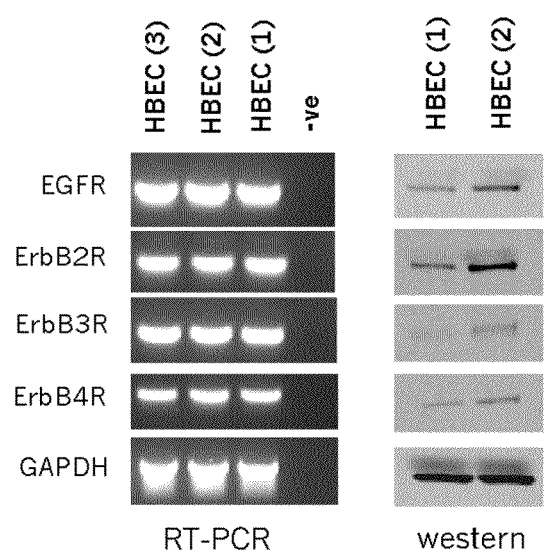

FIG. 9: Analysis of ErB receptor expression in Human Bronchial Epithelial Cells

ErbB receptor expression in primary human bronchial epithelial cells was analysed by RT-PCR (left) and western blot (right). ErbB receptor expression was analysed in 3 or 2 donors for mRNA and protein, respectively. Expression of the housekeeping gene GAPDH is also shown.

Figure 10:
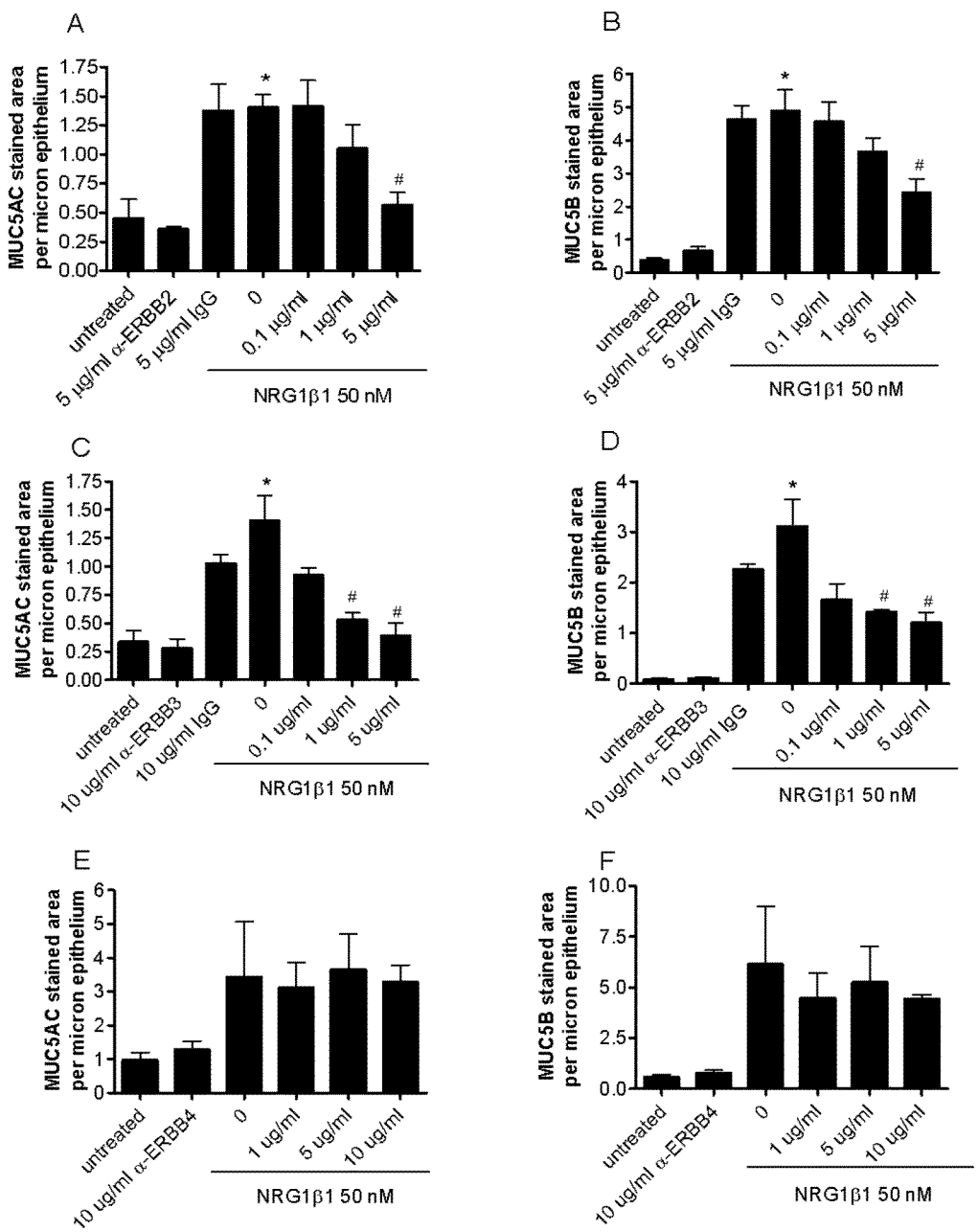

FIG. 10: Effects of ErbB receptor neutralising antibodies on NRG1β1-induced goblet cell formation Effects of anti-ErbB receptor antibodies on NRG1β1-induced MUC5AC protein (A, C, E) and MUC5B protein (B, D, F) in HBECs were quantified by histology. Data for an anti-ErbB2 receptor antibody (A, B), anti-ErbB3 receptor antibody (C, D) and an anti-ErbB4 receptor antibody (E, F) are shown and the concentration of antibody used are indicated on the graphs. * Significant difference from the untreated control ($P<0.05$); # significant difference from the NRG1β1 only treated group ($P<0.05$). The results are shown as the mean±SEM (n=3) and are representative of 2 independent experiments.

5.2 List of Abbreviations

| Abbreviation | Description |
|---|---|
| ALI | Air Liquid Interface |
| BAL | Bronchial Alveolar Lavage |
| BSA | Bovine Serum Albumin |
| BSMC | Bronchial Smooth Muscle Cell |
| CF | Cystic Fibrosis |
| COPD | Chronic Obstructive Pulmonary Disease |
| ELISA | Enzyme-Linked Immunosorbent Assay |
| HBEC | Human Bronchial Epithelial Cells |
| HRG | Heregulin |
| IL-13 | Interleukin 13 |
| MUC5AC | Mucin 5AC |
| MUC5B | Mucin 5B |
| NRG 1 | Neuregulin-1 |
| OVA | Ovalbumin |
| PAS | Periodic Acid-Schiff |
| RT-PCR | Reverse Transcriptase Polymerase Chain Reaction |
| TMB | 3,3',5,5'-Tetramethylbenzidine |
| EGFR | Epidermal Growth Factor Receptor |
| ErbB2 | v-erb-b2 avian erythroblastic leukaemia viral oncogene homolog 2 |

5.3 Methods 5.3.1 Culture of HBECs

Human Bronchial epithelial cells (HBECs; Cambrex) were cultured in bronchial epithelial cell growth medium (BEGM; Cambrex) supplemented with the provided singlequots essentially as described in [Atherton et al, 2003]. For differentiation, cells were grown on 0.4 μm pore size, 12 mm TRANSWELL® inserts (Costar) at a cell density of $8.25 \times 10^4$ cells/insert in differentiation medium. Differentiation medium contained 50% BEGM and 50% Dulbeccos' modified Eagle's medium (DMEM) and was supplemented with 52 μg/ml bovine pituitary extract, 5 μg/ml insulin, 0.5 μg/ml hydrocortisone, 10 μg/ml transferrin, 0.5 μg/ml epinephrine 0.5 ng/ml human EGF, 50 μg/ml gentamicin and 50 nM retinoic acid. Cells were maintained submerged for 7 days then grown at air-liquid interface (ALI) for 7-14 days and medium was replenished every 2-3 days. Cells were treated with NRG1α or NRG1β1 (R&D SYSTEMS®) during the ALI culture period, added to the basolateral chamber of the TRANSWELL® inserts. At all stages cells were maintained at 37° C. in the presence of 5% $CO_2$ in an air incubator.

5.3.2. Immunohistochemical Detection of MUC5AC and MUC5B Protein

After 7 days (unless otherwise stated) of differentiation at ALI, the apical surface of the HBECs was washed gently with PBS and fixed with neutral buffered formalin and wax embedded. Inserts were sectioned at 3 μm thickness and stained with either an anti-MUC5AC antibody (45M1; LABVISION®) or anti-MUC5B monoclonal antibodies using a DABMAP protocol on a VENTANA® XT immunostainer and counter-stained with 1% alcian blue in 3% acetic acid, pH 2.5. The area of staining was assessed using a ZEISS® Axioplan 2 microscope (×10 magnification) with an Imaging Associated KS400 image analyzer (Imaging Associates). Fourteen fields were scored for each sample. Data are presented as goblet cell density, which was defined as the ratio of stained area ($\mu m^2$) to length (μm) of epithelium scored. Custom made anti-MUC5B monoclonal antibodies were obtained from the Hybridoma Core Laboratory, University of Florida and were raised against the peptide SWYNGHRPEPGLG (SEQ ID NO:11).

5.3.3 Preparation of RNA and First Strand cDNA Synthesis

Total RNA was isolated from primary cells as described previously [Jones et al, 2003]. Total RNA was isolated from cells using the RNeasy mini RNA isolation kit (QIAGEN®) according to the manufacturer's instructions. RNA was also isolated from lung tissue from the mouse ovalbumin (OVA) model of allergen-induced goblet cell formation. Balb/c mice had been sensitized with OVA over 2 weeks and given a daily challenge of ovalbumin (50 mg/ml) for 2 consecutive days, as described in [Trifilieff et al, 2000]. RNA was prepared from mouse lung tissue using the reagents and protocols supplied in the QIAGEN® RNeasy miniprep kit. Frozen lung tissue (20 mg) was homogenized in 600 μl of RLT buffer using a POLYTRON® homogenizer (Kinematica AG). Lysates were further processed using Qiashredder columns (QIAGEN®) according to the manufacturer's instructions.

First strand cDNA synthesis was performed using 1 μg of total RNA and the reagents and protocol provided in the first strand cDNA synthesis kit (Roche Diagnostics Ltd.).

5.3.4 Quantitative RT-PCR

MUC5AC and MUC5B gene expression in lung tissue from the mouse OVA model (Section 2-3) was analysed by quantitative RT-PCR. PCR reaction mixtures were prepared in a final volume of 20 μl and contained 10 μl 2×SYBR Green PCR Master Mix (Sigma), 0.8 μl of 10 μM of each forward and reverse primer (final concentration 400 nM) and 4.4 μd$H_2O$. Sixteen μl of this master mix was placed into each well of a 96-well Optical Reaction Plate and 4 μl of cDNA template (Section 2-3) was added to each well. Samples were analysed in duplicate using an ABI7900 Sequence Detection System (APPLIED BIOSYSTEMS®). Primer sequences for MUC5AC, MUC5B and the β-actin housekeeping gene control are shown in Table 1.

A standard curve was included on each plate using a mixed lung cDNA pool with cDNA concentrations in the range 66,666 to 274 pg. A no template control (NTC) was included which contained nuclease free water instead of diluted cDNA The quantitative PCR program was as follows: Stage 1, 50° C. for 2 min; Stage 2, 95° C. for 10 min; Stage 3, 40 cycles of 95° C. for 15 s, 60° C. for 15 s and 72° C. for 30 s. Data were interpreted by the relative method (ABI PRISM 7700 Sequence Detection System. User Bulletin #2, PE APPLIED BIOSYSTEMS®, 1997). Expression values are shown normalised to the housekeeping gene β-actin.

TABLE 1

RT-PCR primers

| Gene | Primer sequences (5' to 3') | Primer names | Length of PCR product (bp) |
|---|---|---|---|
| Trans-ferrin | TTACAGTGGCTGTATTCTGCTGG (SEQ ID NO: 1) TGCTGTTCTCATGGAAGCTATGG (SEQ ID NO: 2) | TransFor TransRev | 401 |

TABLE 1-continued

RT-PCR primers

| Gene | Primer sequences (5' to 3') | Primer names | Length of PCR product (bp) |
|---|---|---|---|
| NRG1β1 | CAAGCATCTTGGGATTGAA (SEQ ID NO: 3) | NRG1β1For | 188 |
|  | TGTTTCGTTCTGACCGAAGG (SEQ ID NO: 4) | NRG1Rev |  |
| Muc5ac | CAGCCGAGAGGAGGGTTTGATCT (SEQ ID NO: 5) | Muc5acFor | 399 |
|  | AGTCTCTCTCCGCTCCTCTCAAT (SEQ ID NO: 6) | Muc5acRev |  |
| Muc5b | AGGAAGACCAGTGTGTTTGTC (SEQ ID NO: 7) | Muc5bFor | 615 |
|  | GTCCTCATTGAAGAAGGGCTG (SEQ ID NO: 8) | Muc5bRev |  |
| β-actin | TGTGATGGTGGGAATGGGTCAG (SEQ ID NO: 9) | MmβactinFor | 514 |
|  | TTTGATGTCACGCACGATTTCC (SEQ ID NO: 10) | MmβactinRev |  |

5.3.5 RT-PCR

For analysis of NRG1β1 gene expression in cDNA prepared from primary human cells. PCR reactions contained 10 µl of 2× HOTSTARTAQ® Master Mix (QIAGEN®), 20 pmol each of NRG1β1For and NRG1Rev primers (Sigma-Genosys; Table 1), 1µl of cDNA template (50 ng) made up in a final volume of 20 µl in 0.2 ml thin walled PCR tubes. Control PCR reactions were performed with primers specific to the housekeeping gene transferrin using primers TransFor and TransRev (Table 1). PCR cycling conditions were as follows: Denaturation at 95° C. for 15 min, 30 cycles of denaturation 94° C. for 15 s, annealing at 55° C. for 15 s, and extension at 72° C. for 45 s, followed by a final extension of 5 min at 72° C. PCR products were analysed on 2% agarose gels and stained with ethidium bromide.

5.3.6 Western Blotting

Western blot analysis was performed on bronchoalveolar lavage (BAL) samples from the mouse OVA model. Samples containing 25 µl of BAL fluid were denatured for 10 min at 70° C. in 1× NuPAGE LDS sample buffer, 50 mM DTT prior to analysis on 4-12% NuPAGE Bis-Tris acrylamide gels at 200 V using the NuPAGE® MOPS running buffer. Gels and buffers were purchased from INVITROGEN®. Samples were transferred onto Immobilon-P PVDF membrane (MILLIPORE®) using NuPAGE® transfer buffer (INVITROGEN®) at 10 V overnight. Membranes were blocked in PBS, 0.1%(v/v) tween-20, 5% (w/v) Blotto milk powder (SANTA CRUZ BIOTECHNOLOGY®) for 1 h at room temperature. Blocking buffer was removed and membranes incubated at room temperature for 3 h with anti-NRG1β1 (sc-347; SANTA CRUZ BIOTECHNOLOGY®) primary antibody diluted 1:600 in blocking buffer. Membranes were washed 4 times for 10 min in wash buffer (PBS, 0.1% (v/v) tween-20) at room temperature with shaking. Blots were incubated in the dark for 1 h with shaking with goat anti-rabbit IRDye800 secondary antibody (Tebu-bio) diluted 1:2000 in 0.5×PBS, 0.05% (v/v) tween-20, 0.5× Odyssey blocking buffer, 0.01% (w/v) SDS. Membranes were washed as described previously and analysed using a LI-COR® Odyssey Infrared imaging system (LI-COR® Biosciences) at 169 µm resolution, focus offset of 3.0 mm and intensity setting of 5.0. NRG1α or NRG1β1 control proteins (LABVISION®) were included as positive controls.

5.3.7 NRG1 beta1 ELISA

NRG1β1 protein levels in BAL fluid of OVA challenged mice (Section 2-3) were analysed using the NRG1β1 DuoSet ELISA kit (R&D SYSTEMS®) using the reagents supplied in the kit. Immuno plates (96-well; NUNC) were coated overnight at room temperature with 100 µl/well mouse anti-human NRG1β1 at 4 µg/ml. Plates were washed 4 times with 400 µl/well of wash buffer (PBS, 0.05% (v/v) tween-20). Plates were blocked for 1 h at room temperature with 300 of buffer A (PBS, 1% (w/v) BSA), then washed as described previously. BAL fluid samples (100 µl/well) or NRG1β1 protein standard diluted in buffer A (0.0625-4 ng/ml) were added to the wells and incubated for 2 h at room temperature. A blank containing buffer A was also included on the plate. The plate was washed as described previously before adding 100 µl/well of detection antibody, biotinylated goat anti-human NRG1β1, at 200 ng/ml for 2 h at room temperature. The plate was washed again and 100 µl/well streptavidin conjugated to horseradish peroxidase (100 µl/well) was added at 1:200 dilution in buffer A for 30 min at room temperature. 3,3',5,5'-Tetramethylbenzidine (TMB) substrate (SIGMA®; 100 µl/well) was added to the plate and incubated for 30 min at room temperature. The reaction was stopped by adding 50 µl/well of 1 M sulphuric acid. The absorbance at 450 nm, corrected for background measured at 540 nm, was measured using a SpectraMax® 340 plate reader (MOLECULAR DEVICES®). Samples were analysed in duplicate.

5.3.8 Data Analysis and Statistics

Data is shown as the mean±SEM and represents duplicate samples from 2 independent experiments. Two sample t-tests were performed to determine if there were significant differences between control and treatment groups (*P<0.05, **P<0.001).

5.4 Results

5.4.1 Effects of NRG1 Alpha and Beta1 on Mucin Expression and Goblet Cell Formation In cultures of primary human bronchial epithelial Cells (HBECs) grown at ALI NRG1β1 treatment caused a dose-dependent increase in MUC5AC protein, a marker for airway goblet cells, as assessed by histology (FIG. 1A). At 50 nM NRG1β1, a 3-fold increase in MUC5AC protein over vehicle levels was obtained. A closely related NRG1 isoform, NRG1α, did not have a significant effect on MUC5AC protein at concentrations of up to 250 nM (FIG. 1B). HBEC inserts stained with the MUC5AC antibody were also counterstained with alcian blue. Interestingly, several alcian blue stained cells which did not stain with the MUC5AC (45M1) antibody were noted in the NRG1β1 treated samples (FIG. 1C), which might reflect the presence of other mucins such as MUC5B. To confirm any effects of NRG1β1 and NRG1α on MUC5B protein, cells were also stained with a monoclonal antibody against MUC5B. Both NRG1 isoforms caused a dose-dependent increase in MUC5B protein up to a concentration of 50 nM (FIG. 2). At 50 nM, NRG1β1 and NRG1α caused a 9.8 and 6.4-fold increase in MUC5B protein respectively. As the NRG1β1 isoform had the most pronounced effects on MUC5AC and MUC5B protein, further studies focused on the NRG1β1.

The effects of NRG1β1 on MUC5AC and MUC5B protein expression over a time course is shown in FIG. 3. Expression of MUC5AC and MUC5B protein was significant compared to vehicle treated controls after 7, 10 or 14 days of NRG1β1 treatment. (FIG. 3).

The gene expression profile of NRG1β1 was analysed in several primary cells. NRG1β1 was found to be expressed in differentiated primary human bronchial epithelial cells (HBECs), bronchial smooth muscle cells (BSMC) and lung fibroblasts (FIG. 4). No expression was detected in T-cells or neutrophils.

Lung tissue from mice challenged with OVA or saline was analysed by quantitative RT-PCR for MUC5AC and MUC5B gene expression. A 57-fold increase in MUC5AC gene expression was observed after OVA challenge (FIG. 5) compared to saline controls. MUC5B gene expression also increased 3-fold after OVA challenge (FIG. 5).

NRG1β1 protein expression in BAL fluid from OVA challenged mice was analysed by western blot. An increase in NRG1β1 protein was detected in BAL fluid from OVA challenged mice compared to saline challenged control mice (FIG. 6). NRG1β1 protein in BAL fluid of OVA challenged mice was quantified by ELISA. A 9-fold increase in NRG1β1 was detected in BAL fluid of OVA challenged mice compared to saline challenged control mice (FIG. 7), consistent with the western blot data. Concentrations of NRG1β1 were around 0.9 ng/ml.

5.4.2 Discussion

The mucins MUC5AC and MUC5B are the predominant component of airway secretions in patients with asthma and COPD [Rose and Voynow, 2006; Rogers, 2003]. In the airways of asthmatics, COPD and CF patients increased numbers of goblet cells have been reported [Aikawa et al, 1992; Ordonez et al, 2001; Saetta et al, 2000; Gronenberg et al, 2002b]. Increased numbers of goblet cells in the airways can be modeled in the mouse OVA model of antigen-induced inflammation. A single or repeated challenged of OVA results in an increase in alcian blue/PAS stained goblet cells in the airways [Trifilieff, El-Hasim and Bertrand, 2000]. We have shown in this report a significant increase in expression of mucins genes MUC5AC and MUC5B in mouse lungs after OVA challenge. This data is consistent with published data where an increase in MUC5AC gene expression in the OVA model was detected by northern blot analysis [Zhudi Alimam et al, 2000].

We have also shown that NRG1β1 induces MUC5AC and MUC5B protein expression in differentiated HBEC cultures, both markers of airway goblet cells. NRG1β1 rather than the closely related isoform NRG1α, had the most pronounced effect on MUC5AC and MUC5B in the in vitro model of goblet cell formation. To further understand the role of NRG1β1 in goblet cell formation in vivo, NRG1β1 protein was analysed in BAL fluid from OVA challenged mice. An increase in NRG1β1 protein was detected by western blot and quantified by ELISA, accompanied by increases in MUC5AC and MUC5B gene expression in the lungs of OVA challenged mice. NRG1 has previously been shown to stimulate differentiation of human airway epithelia and to cause an increase in goblet cell number in human airway epithelial cultures [Vermeer et al, 2006]. However, the NRG1β1 isoform was not investigated in the study of Vermeer et al. and no effects on the mucins MUC5AC and MUC5B reported. NRG1β1 was found in this current study to be expressed in lung-derived cells which included bronchial epithelial cells, bronchial smooth muscle cells and lung fibroblasts.

Thus we have shown that the mucin genes MUC5AC and MUC5B are increased in lungs of OVA challenged mice and this is accompanied by an increase in NRG1β1 protein in the airways. We have also shown that NRG1β1 is potent mediator of MUC5AC and MUC5B-positive goblet cells in vitro and therefore NRG1β1 may represent a potential therapeutic target for respiratory diseases such as asthma, COPD and CF where mucus hypersecretion plays a role.

5.5—Interaction Between NRG1β1 and ErbB 5.5.1 Methods 5.5.1.1 Compound and Antibody Treatment of Cells Compounds or antibodies were diluted in HBEC differentiation medium and added to the basolateral chamber of HBECs grown on TRANSWELL® inserts 2 h prior to the addition of NRG1β1. HBECs were treated with compound or antibody in combination with NRG1β1 for 7 days at ALI, replacing the NRG1β1 together with fresh antibody or compound every time the medium was replenished (every 2-3 days). For each treatment at least 3 identical wells were prepared. ErbB2 receptor (AF1129) and ErbB3 receptor antibodies (MAB3841) were from R&D SYSTEMS® and ErbB4 receptor antibody (MS-304-PIABX) was from LAB VISION® Corporation.

5.5.1.2 RT-PCR Analysis of ErbB Receptor Expression

For analysis of ErbB receptor expression in cDNA prepared from differentiated HBECs, PCR reactions were prepared as follows: PCR reaction mixtures contained 12.5 μl HOTSARTAQ® Master mix (QIAGEN®), 50 pmol of each forward and reverse primer (Table 2), 50 ng cDNA and water to a final volume of 25 μl in 0.2 ml thin-walled PCR tubes. Control PCR reactions were performed with primers specific to the housekeeping gene GAPDH using primers GAPDHF and GAPDHR (Table 2). PCR cycling conditions were as follows: Denaturation at 95° C. for 15 min, 35 cycles of denaturation 94° C. for 15 s, annealing at 55° C. for 15 s, and extension at 72° C. for 45 s, followed by a final extension of 5 min at 72° C. PCR products were analysed on 2% agarose gels and stained with ethidium bromide.

TABLE 2

RT-PCR primers for analysis of ErbB receptor expression

| Gene | Primer sequences (5' to 3') | Primer names | Length of PCR product (bp) |
| --- | --- | --- | --- |
| ErbB1 | gtcctcattgccctcaacacag (SEQ ID NO: 12) | ErbB1F | 326 |
|  | ccattgggacagcttggatcac (SEQ ID NO: 13) | ErbB1R |  |
| ErbB2 | cagttaccagtgccaatatcc (SEQ ID NO: 14) | ErbB2F | 250 |
|  | ttgtgcagaattcgtcccc (SEQ ID NO: 15) | ErbB2R |  |
| ErbB3 | actctgaatggcctgagtg (SEQ ID NO: 16) | ErbB3F | 253 |
|  | caaacttcccatcgtagacc (SEQ ID NO: 17) | ErbB3R |  |
| ErbB4 | ACCAGCATTGAGCACAACC (SEQ ID NO: 18) | ErbB4F | 368 |
|  | CGTCCACATCCTGAACTACC (SEQ ID NO: 19) | ErbB4R |  |
| GAPDH | CCACCCATGGCAAATTCCATGGCA (SEQ ID NO: 20) | GAPDHF | 598 |
|  | TCTAGACGGCAGGTCAGGTCCACC (SEQ ID NO: 21) | GAPDHR |  |

5.5.1.3 Western Blot Analyses of ErbB Receptor Expression

Cells were lysed in ice-cold lysis buffer which contained 50 mM Tris pH 7.5, 150 mM NaCl, 0.65% v/v NP-40 supplemented with Complete protease inhibitor cocktail (ROCHE®) and lysates cleared by centrifugation at 16000×g for 5 min at 4° C. Protein concentration was determined using a Micro BCA Protein Assay Kit (PERBIO®) according to the manufacturer's instructions. Cleared lysates were denatured at 70° C. for 10 min in 1× NuPAGE sample buffer (INVITROGEN®) and equal amounts of protein from samples resolved using Bis-Tris NuPAGE polyacrylamide gels with MOPS running buffer (INVITROGEN®). Proteins were transferred to Immobilon-P PVDF membranes (MILLIPORE®) in NuPAGE transfer buffer (INVITROGEN®). Primary antibodies were used at 1/1000 dilution and appropriate secondary antibodies at 1/2000 or 1/5000 dilution. All primary antibodies were from SANTA CRUZ BIOTECHNOLOGY® and were rabbit polyclonal antibodies, except where indicated as follows: EGFR (1005); ErbB2 (C-18), ErbB3 (C-17), ErbB4 (C-18) and GAPDH, a mouse monoclonal primary antibody (6C5). The secondary antibodies were Alexa Fluor 680 conjugated anti-rabbit secondary antibody (INVITROGEN®) or IRDye 800 conjugated anti-mouse secondary antibody (Tebu-bio). Membranes were incubated in blocking buffer (PBS containing 0.1% v/v tween-20 and 5% w/v Blotto (SANTA CRUZ BIOTECHNOLOGY®) for 4 h at room temperature followed by overnight incubation at 4° C. with primary antibodies diluted in blocking buffer. Membranes were washed with washing buffer (PBS, 0.1% v/v tween-20) before incubation with respective infrared-dye conjugated secondary antibodies diluted in Odyssey blocking buffer (50% v/v PBS: 50% v/v Odyssey buffer (LI-COR® Biosciences UK Ltd) supplemented with 0.1% v/v tween-20 and 0.01% w/v SDS at room temperature for 1 h in the dark. Following incubation with the secondary antibodies, membranes were again washed in the dark before being imaged using a LI-COR® Odyssey infrared imaging system at 169 μm resolution, focus offset of 3.0 mm and intensity setting of 5.0.

5.6 Results 5.6.1 Effects of a pan-ErbB Receptor Inhibitor on Goblet Cell Formation The effects of a pan-ErbB receptor inhibitor on NRG1β1-induced goblet cell formation were analyzed. HBECs were pre-treated with inhibitor prior to addition of NRG1β1 and cells were then grown for 7 days at ALI. The effects on the goblet cell markers MUC5AC and MUC5B were analyzed by histology. The NRG1β1-induced increases in MUC5AC and MUC5B protein were significantly inhibited by the pan-ErbB receptor inhibitor at 10 μM (FIG. 8).

5.6.2 Effects of Anti-ErbB Receptor Antibodies on NRG1β1-Induced Goblet Cell Formation The ErbB receptor expression profile was analysed in HBECs from multiple human donors. Protein and mRNA for all four ErbB receptor family members EGFR, ErbB2, ErbB3 and ErbB4 could be detected in samples from multiple primary human bronchial epithelial cell donors (FIG. 9).

The ErbB receptor involved in NRG1β1-induced goblet cell formation was assessed using neutralising antibodies against either ErbB2, ErbB3 or ErbB4 receptors in the primary human bronchial epithelial cell model of goblet cell formation. HBECs were pre-treated with antibody prior to NRG1β1 treatment at ALI for 7 days. Antibodies against the ErbB2 and ErbB3 receptors inhibited NRG1β1-induced MUC5AC and MUC5B production, whereas an antibody against ErbB4 had no effect (FIG. 10).

5.6.3 Discussion

NRG1β1 has been reported to signal through ErbB2/ErbB3 or ErbB2/ErbB4 heterodimers [Falls, 2003; Citri et al, 2003]. Expression analyses indicated that all of the ErbB receptor family members, EGFR, ErbB2-ErbB4 were expressed on primary human bronchial epithelial cells. To further delineate which receptors are involved in NRG1β1-induced goblet cell formation, a pan-ErbB receptor tyrosine kinase inhibitor [Traxler et al, 2004] was analysed in an in vitro goblet cell formation assay. The pan-ErbB receptor tyrosine inhibitor significantly reduced expression of the goblet cell mucins MUC5AC and MUC5B, indicating ErbB receptor involvement in this process. To further dissect which ErbB receptor was responsible for the NRG1β1-induced goblet cell formation, neutralising antibodies against the ErbB2, ErbB3 and ErbB4 receptors were tested. Neutralising antibodies against ErbB2 and ErbB3 significantly reduced NRG1β1-induced goblet cell formation, as indicated by the goblet cell markers MUC5AC and MUC5B. In contrast, the anti-ErbB4 receptor neutralising antibody had no effect on NRG1β1-iduced goblet cell formation. This data suggests that the ErbB2 and ErbB3 receptors are involved in NRG1β1-induced goblet cell formation in human airway epithelial cells.

6. REFERENCES

[Aikawa T, Shimura S, Sasaki H, et al (1992)] Marked Goblet Cell Hyperplasia with mucus accumulation in the airways of patients who died of severe acute asthma attack. Chest; 101:916-922.

[Atherton C, Jones G and Danahay H (2003)] IL-13-induced changes in the goblet cell density of human bronchial epithelial cell cultures:MAP kinase and phosphatidtylinositol 3-kinase regulation. Am J Physiol Lung Cell Mol Physiol; 285:L730-L739.

[Boucher R C (2002)] An overview of the pathogenesis of cystic fibrosis lung disease. Adv Drug Del Rev; 54:1359-1371.

[Caramori G, Di Gregorio C, Carlstedt I, et al (2004)] Mucin expression in peripheral airways of patients with chronic obstructive pulmonary disease.Histopathology; 45:477-484.

[Citri A, Skaria K B and Yarden Y (2003)] The deaf and dumb: the biology of ErbB-2 and ErbB-3. Exp Cell Res; 284: 54-65.

[deBoer W I, Hau C M, van Schadewijk A, et al (2006)] Expression of the Epidermal Growth Factors and Their Receptors in Bronchial Epithelium of subjects with Chronic Obstructive Pulmonary Disease. Am J Clin Path; 125:184-192.

[Falls D L (2003)] Neuregulins: functions, forms and signalling strategies. Exp Cell Res; 284: 14-30.

[Dammann C E L, Nielsen H C and Carraway III K L (2003)] Role of Neuregulin-1α in the Developing Lung. Am J Resp Crit Care Med; 167:1711-1716.

[Gronenberg D A, Eynott P R, Lim S, et al (2002a)] Expression of respiratory mucins in fatal status asthmaticus and mild asthma. Histopathology; 40:367-373.

[Gronenberg D A, Eynott P R, Oates T, et al (2002b)] Expression MUC5AC and MUC5B mucins in normal and cystic fibrosis lung. Resp Med; 96:81-86.

[Hays S R and Fahy J V (2003)] The role of mucus in fatal asthma. Am J Med; 115:68-69.

[Henke M O, Renner A, Huber R M, et al (2004)] MUC5AC and MUC5B mucins are decreased in cystic fibrosis airway secretions. Am J Resp Cell Mol Biol; 31:86-91.

[Henke M O, John G, Germann M, et al (2007)] MUC5AC and MUC5B mucins increase in cystic fibrosis airway secretions during pulmonary exacerbation. Am J Resp Crit Care Med; 175:816-821.

[Hogg J C, Chu F, Utokaparch S, et al (2004)] The nature of small airway obstruction in chronic obstructive pulmonary disease. N Engl J Med; 350:2645-2653.

[Holmes W E, Sliwkowski M X, Alcita R W, et al (1992)] Identification of heregulin, a specific activator pf p185erbB2. Science; 256:1205-1209.

[Jones C E, Holden S, Tenaillon L, et al (2003)] Expression and Characterisation of a 5-oxo-6E,8Z,11Z,14Z-Eicoastetraenoic Acid Receptor Highly Expressed on Human Eosinophils and Neutrophils. Mol Phamacol; 63:471-477.

[Jones J T, Akita R W and Sliwkowski M X (1999)] Binding specificities and affinities of egf domains for ErbB receptors. FES Letts; 447:227-231.

[Kirkham S, Sheehan J K, Knight D, et al (2002)] Heterogeneity of airways mucus: variations in the amounts and glycoforms of the major oligomeric mucins MUC5AC ad MUC5B. Biochem J; 361:537-546.

[Kuperman D A, HuangX, Koth L L, et al (2002)] Direct effects of interleukin-13 on epithelial cells cause airway hyperreactivity and mucin overproduction in asthma. Nature Med; 8:885-889.

[Kuyper L M, Pare P D, Hogg J C, et al (2003)] Characterization of airway plugging in fatal asthma. Am J Med; 115:6-11.

[Ordonez C L, Khashayar R, Wong H H, et al (2001)] Mild and Moderate asthma is associated with airway goblet cell hyperplasia and abnormalities in mucin gene expression. Am J Resp Crit Care Med; 163:517-523.

[Patel N V, Acarregui M J, Snyder J M, et al (2000)] Neuregulin-1 and human epidermal growth factor receptors 2 and 3 play a role in human lung development in vitro. Am J Resp Cell Mol Biol; 22:432-440.

[Prescott E, Lange P and Vestbo J (1995)] Chronic mucus hypersecretion in COPD and death from pulmonary infection. Eur Resp J; 8:1333-1338.

[Rogers D F (2003)] The airway goblet cell. Int J Biochem Cell Biol; 35:1-6.

[Rose M C and Voynow J A (2006)] Respiratory tract mucin genes and mucin glycoproteins in health and disease. Physiol Rev; 86:245-278.

[Saetta M, Turato G, Baraldo S, et al (2000)] Goblet cell hyperplasia and epithelial inflammation in peripheral airways of smokers with both symptoms of chronic bronchitis and chronic airflow limitation. Am J Resp Crit Care Med; 161: 1016-1021.

[Traxler P, Allegrini P R, Brandt R, et al (2004)] AEE788: A dual family epidermal growth factor receptor/ErbB2 and vascular endothelial growth factor receptor tyrosine kinase inhibitor with antitumor and antiangiogenic activity. Cancer Res; 64:49 31-4941.

[Trifilieff A, El-Hashim A and Bertrand C (2000)] Time course of inflammatory and remodeling events in a murine model of asthma: effect of steroid treatment. Am J Physiol Lung Cell Mol Physiol; 279:L1120-L1128.

[Vermeer P D, Einwalter L A, Moninger T O, et al (2003)] Segregation of receptor and ligand regulates activation of epithelial growth factor receptor. Nature; 422:322-326.

[Vermeer P D, Panko L, Karp P, et al (2006)] Differentiation of human airway epithelia is dependent on erbB2. Am J Physiol Lung Cell Mol Physiol; 291:L175-L180.

[Vestbo J (2002)] Epidemiological studies in mucus hypersecretion. Novartis Foundation Symposium; 248:3-19.

[Vestbo J, Prescott E and Lange P (1996)] Association of chronic mucus hypersecretion with FEV 1 decline and chronic obstructive pulmonary disease morbidity. Am J Resp Crit Care Med; 153:1530-1535.

[Williams O W, Sharafkhanaeh A, Kim V, et al (2006)] Airway mucus. From production to secretion. Am J Resp Cell Mol Biol; 34:527-536.

[Wills-Karp M, Luyimbazi J, Xu X, et al (1998)] Interleukin-13: Central Mediator of Allergic Asthma. Science; 282: 2258-2261.

[Zhu Z, Homer R J, Wang Z, et al (1999)] Pulmonary expression of interleukin-13 causes inflammation, mucus hypersecretion, subepithelial fibrosis, physiologic abnormalities, and eotaxin production. J Clin Invest; 103:779-788.

[Zhuhdi Alimam M, Piazza F M, Selby D M, et al (2000)] Muc-5/5ac Mucin messenger RNA and Protein Expression is a Marker of Goblet Cell Metaplasia In Murine Airways. Am J Resp Cell Mol Biol; 22:253-260.

Almeida and Allshire (2005), TRENDS Cell Biol., 15:251-258. Waterhouse et al. (1998), Proc. Natl. Acad. Sci. USA, 95:13959-13964.

Smith et al. (2000), Nature, 407:3 19-320.

Pasquinelli et al. (2005), Curr. Opin. Genet. Develop., 15:200-205.

Millar and Waterhouse (2005), Funct. Integr. Genomics, 5:129-135.

---

The invention claimed is:

1. A method of treating a patient afflicted with a respiratory disease or disorder featuring aberrant mucus production, wherein the method comprises the step of:
   administering to said patient a therapeutically effective amount an antibody which inhibits the interaction between Neuregulin-1 β1(NRG1 β1) and a cognate receptor to inhibit goblet cell hyperplasia.

2. The method of claim 1 wherein the antibody binds to NRG1β1.

3. The method of claim 1 wherein the antibody binds ErbB2, ErbB3, or the ErbB2/ErbB3 heterodimer.

4. The method of claim 1, wherein the disease featuring aberrant mucus production is selected from the group consisting of: COPD, cystic fibrosis (CF), chronic bronchitis, and asthma.

5. A method of treating a patient afflicted with a respiratory disease or disorder characterized by aberrant mucus production which method comprises the step of:
   co-administering an antibody that inhibits the interaction between NRG1β1 and ErbB2, ErbB3, and/or the ErbB2/ErbB3 heterodimer, together with:
   one or more agents selected from the group consisting of:
   an anti-human IL-13 agent which inhibits the interaction between human IL-13 and its cognate human receptor; an anti-human IL-4 agent which inhibits the interaction between human IL-45 and its human IL-4 receptor; an anti-human IL-5 agent which inhibits the interaction between human IL-5 and its cognate receptor; and/or an anti-IgE agent which inhibits the interaction between human IgE and its cognate receptor.

* * * * *